United States Patent [19]

Hauptmann et al.

[11] Patent Number: 5,618,988
[45] Date of Patent: Apr. 8, 1997

[54] ENHANCED CAROTENOID ACCUMULATION IN STORAGE ORGANS OF GENETICALLY ENGINEERED PLANTS

[75] Inventors: Randal Hauptmann, Woodland, Calif.; William H. Eschenfeldt, St. Charles, Ill.; Jami English, Aurora, Ill.; Friedhelm L. Brinkhaus, Lisle, Ill.

[73] Assignee: Amoco Corporation, Chicago, Ill.

[21] Appl. No.: 331,004

[22] Filed: Oct. 28, 1994

Related U.S. Application Data

[63] Continuation-in-part of Ser. No. 805,061, Dec. 9, 1991, abandoned, and Ser. No. 93,577, Jul. 19, 1993, which is a continuation of Ser. No. 785,569, Oct. 30, 1991, abandoned, and a continuation-in-part of Ser. No. 96,043, Jul. 22, 1993, Pat. No. 5,530,189, which is a continuation of Ser. No. 785,568, Oct. 30, 1991, abandoned, and a continuation-in-part of Ser. No. 95,726, Jul. 21, 1993, Pat. No. 5,530,188, which is a continuation of Ser. No. 785,566, Oct. 30, 1991, abandoned, and a continuation-in-part of Ser. No. 96,623, Jul. 22, 1993, abandoned, which is a continuation of Ser. No. 805,061, which is a continuation-in-part of Ser. No. 562,674, Aug. 3, 1990, abandoned, Ser. No. 785,569, Ser. No. 785, 568, Ser. No. 785,566, and Ser. No. 662,921, Feb. 28, 1991, abandoned, said Ser. No. 562,674, Aug. 30, 1990, is a continuation-in-part of Ser. No. 562,551, May 18, 1990, abandoned, which is a continuation-in-part of Ser. No. 487,613, Mar. 2, 1990, abandoned.

[51] Int. Cl.⁶ ........................................ A01H 4/00
[52] U.S. Cl. ................ 800/205; 800/255; 800/DIG. 46; 435/172.3
[58] Field of Search .................... 800/205, 255, 800/DIG. 46; 435/320.1, 172.3, 69.1

[56] References Cited

U.S. PATENT DOCUMENTS

| | | | |
|---|---|---|---|
| 5,023,179 | 11/1988 | Lam et al. | 435/172.3 |
| 5,110,732 | 3/1989 | Benfey et al. | 435/172.3 |
| 5,304,478 | 4/1994 | Bird et al. | 435/172.3 |

FOREIGN PATENT DOCUMENTS

| | | |
|---|---|---|
| 1393690 | 10/1990 | European Pat. Off. . |
| WO88/02405 | 4/1988 | WIPO . |
| WO91/13992 | 9/1991 | WIPO . |
| WO91/13078 | 9/1991 | WIPO . |

OTHER PUBLICATIONS

*Cartotenoids as Colorants and Vitamin A Precursors*, J.C. Bauernfeind, ed., Chapter 2 "Carotenoids as Food Color", H. Klaui and J.C. Bauernfeind, Academic Press, New York (1981) pp. 48–317.

Chamovitz et al., *J. Biol. Chem.*, 268(23):17348–17353 (1993).
T.W. Goodwin, "Carotenoids" in *Encyclopedia of Plant Physiology*, New Series, vol. 8, Pirson et al., eds. Secondary Plant Products, Chapter 5.3, Bell et al., eds, Springer–Verlag, New York (1980) pp. 257–287.
Fray et al., *Plant Mol. Biol.*, 22:589–692 (1993).
Finnegan et al., *Bio/Technology*, 12:883–888 (Sep. 1994).
Perry et al., *J. Bacteriol.*, 168:607 (1986).
Armstrong et al., *Mol. Gen. Genet.*, 216:254–268 (1989).
Armstrong et al., *J. Biol. Chem.*, 265(14):8329–8338 (1990).
Schnurr et al., *FEMS Microbiol. Lett.*, 78:157–162 (1991).
Bartley et al., *J. Biol. Chem.*, 267(8):5036–5039 (1992).
Romer et al., *Biochem. Biophys. Res. Commun.*, 196(3):1414–1421 (1993).
Chamovitz et al., *FEBS Lett.*, 296(3):305–310 (1992).
von Heijne et al., *Eur. J. Biochem.*, 180:535–545 (1989).
della–Cioppa et al., *Plant Physiol.*, 84:965–968 (1987).
Shah et al., *Science*, 233:478–481 (1986).
DiRita and Gelvin, *Mol. Gen. Genet.*, 107:233–241 (1987).
Yamamoto et al., *Plant Cell*, 3:371–381 (1991).
Deikman et al., *EMBO J.*, 7(11):3315–3320 (1988).
Deikman et al., *Plant Physiol.*, 100:2013–2017 (1992).
Yang et al., *Proc. Natl. Acad. Sci., USA*, 87:4144–4148 (1990).
Twell et al., *Plant Mol. Biol.*, 9:365–375 (1987).
Wenzler et al., *Plant Mol. Biol.*, 12:41–50 (1989).
Benfey et al., *Science*, 244:174–181 (1988).
Schardl et al., *Gene*, 61:1–11 (1987).
Dong et al., *Bio/Technology*, 9:858–863 (1991).
Wang et al., *Bio/Technology*, 10:691–696 (1992).
Vasil et al., *Bio/Technology*, 10:667–674 (1992).
Horsch et al., *Science*, 227:1229–1231 (1985).
Brown et al., *J. Amer. Soc. Hort. Sci.*, 118(1):145–150 (1993).

*Primary Examiner*—Che S. Chereskin
*Attorney, Agent, or Firm*—Amoco Corporation

[57] ABSTRACT

A transgenic higher plant, seed containing the transgene, and methods of providing enhanced carotenoid accumulation are disclosed. The transgenic higher plant has a genomic structural gene that encodes a chimeric polypeptide conjugate and over accumulates a colored native carotenoid in a preselected storage organ relative to the accumulation in a non-transgenic plant of the same type. Expression of the chimeric polypeptide is driven by a promoter operatively linked to that structural gene that provides storage organ-enhanced expression. The chimeric polypeptide has an N-terminal plastid transit peptide portion whose C-terminus is linked to the N-terminus of a non-higher plant phytoene synthase enzyme.

38 Claims, 13 Drawing Sheets

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
    ( A ) LENGTH: 1083 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:1:

```
GCATGAGCCA  ACCGCCGCTG  CTTGACCACG  CCACGCAGAC  CATGGCCAAC  GGCTCGAAAA    60
GTTTTGCCAC  CGCTGCGAAG  CTGTTCGACC  CGGCCACCCG  CCGTAGCGTG  CTGATGCTCT   120
ACACCTGGTG  CCGCCACTGC  GATGACGTCA  TTGACGACCA  GACCCACGGC  TTCGCCAGCG   180
AGGCCGCGGC  GGAGGAGGAG  GCCACCCAGC  GCCTGGCCCG  GCTGCGCACG  CTGACCCTGG   240
CGGCGTTTGA  AGGGCCGAG   ATGCAGGATC  CGGCCTTCGC  TGCCTTTCAG  GAGGTGGCGC   300
TGACCCACGG  TATTACGCCC  CGCATGGCGC  TCGATCACCT  CGACGGCTTT  GCGATGGACG   360
TGGCTCAGAC  CCGCTATGTC  ACCTTTGAGG  ATACGCTGCG  CTACTGCTAT  CACGTGGCGG   420
GCGTGGTGGG  TCTGATGATG  GCCAGGGTGA  TGGGCGTGCG  GGATGAGCGG  GTGCTGGATC   480
GCGCCTGCGA  TCTGGGGCTG  GCCTTCCAGC  TGACGAATAT  CGCCCGGGAT  ATTATTGACG   540
ATGCGGCTAT  TGACCGCTGC  TATCTGCCCG  CCGAGTGGCT  GCAGGATGCC  GGGCTGACCC   600
CGGAGAACTA  TGCCGCGCGG  GAGAATCGGG  CCGCGCTGGC  GCGGGTGGCG  GAGCGGCTTA   660
TTGATGCCGC  AGAGCCGTAC  TACATCTCCT  CCCAGGCCGG  GCTACACGAT  CTGCCGCCGC   720
GCTGCGCCTG  GGCGATCGCC  ACCGCCCGCA  GCGTCTACCG  GGAGATCGGT  ATTAAGGTAA   780
AAGCGGCGGG  AGGCAGCGCC  TGGGATCGCC  GCCAGCACAC  CAGCAAAGGT  GAAAAAATTG   840
CCATGCTGAT  GGCGGCACCG  GGGCAGGTTA  TTCGGGCGAA  GACGACGAGG  GTGACGCCGC   900
GTCCGGCCGG  TCTTTGGCAG  CGTCCCGTTT  AGGCGGGCGG  CCATGACGTT  CACGCAGGAT   960
CGCCTGTAGG  TCGGCAGGCT  TGCGGGCGTA  AATAAAACCG  AAGGAGACGC  AGCCCTCCCG  1020
GCCGCGCACC  GCGTGGTGCA  GGCGGTGGGC  GACGTAGAGC  CGCTCCGTAG  CCGTCGGGTC  1080
GAC                                                                    1083
```

( 2 ) INFORMATION FOR SEQ ID NO:2:

( i ) SEQUENCE CHARACTERISTICS:
    ( A ) LENGTH: 309 amino acids
    ( B ) TYPE: amino acid
    ( D ) TOPOLOGY: linear ( i i ) MOLECULE TYPE: protein ( x i ) SEQUENCE DESCRIPTION: SEQ ID NO:2:

```
Met  Arg  Gln  Pro  Pro  Leu  Leu  Asp  His  Ala  Met  Gln  Thr  Met  Ala  Asn
 1                  5                        10                       15

Gly  Ser  Lys  Ser  Phe  Ala  Thr  Ala  Ala  Lys  Leu  Phe  Asp  Pro  Ala  Thr
              20                       25                       30

Arg  Arg  Ser  Val  Leu  Met  Leu  Tyr  Thr  Trp  Cys  Arg  His  Cys  Asp  Asp
         35                       40                       45

Val  Ile  Asp  Asp  Gln  Thr  His  Gly  Phe  Ala  Ser  Glu  Ala  Ala  Ala  Glu
```

|     | 50  |     |     |     |     | 55  |     |     |     |     | 60  |     |     |     |
|-----|-----|-----|-----|-----|-----|-----|-----|-----|-----|-----|-----|-----|-----|-----|
| Glu | Glu | Ala | Thr | Gln | Arg | Leu | Ala | Arg | Leu | Arg | Thr | Leu | Thr | Leu | Ala |
| 65  |     |     |     |     | 70  |     |     |     |     | 75  |     |     |     |     | 80  |

Glu Glu Ala Thr Gln Arg Leu Ala Arg Leu Arg Thr Leu Thr Leu Ala
65                          70                      75                              80

Ala Phe Glu Gly Ala Glu Met Gln Asp Pro Ala Phe Ala Ala Phe Gln
            85                      90                          95

Glu Val Ala Leu Thr His Gly Ile Thr Pro Arg Met Ala Leu Asp His
            100             105                     110

Leu Asp Gly Phe Ala Met Asp Val Ala Gln Thr Arg Tyr Val Thr Phe
            115             120                     125

Glu Asp Thr Leu Arg Tyr Cys Tyr His Val Ala Gly Val Val Gly Leu
        130             135                     140

Met Met Ala Arg Val Met Gly Val Arg Asp Glu Arg Val Leu Asp Arg
145                     150                 155                         160

Ala Cys Asp Leu Gly Leu Ala Phe Gln Leu Thr Asn Ile Ala Arg Asp
                165             170                     175

Ile Ile Asp Asp Ala Ala Ile Asp Arg Cys Tyr Leu Pro Ala Glu Trp
            180                 185                     190

Leu Gln Asp Ala Gly Leu Thr Pro Glu Asn Tyr Ala Ala Arg Glu Asn
        195                 200                     205

Arg Ala Ala Leu Ala Arg Val Ala Glu Arg Leu Ile Asp Ala Ala Glu
    210                 215                     220

Pro Tyr Tyr Ile Ser Ser Gln Ala Gly Leu His Asp Leu Pro Pro Arg
225                 230                     235                         240

Cys Ala Trp Ala Ile Ala Thr Ala Arg Ser Val Tyr Arg Glu Ile Gly
            245                 250                     255

Ile Lys Val Lys Ala Ala Gly Gly Ser Ala Trp Asp Arg Arg Gln His
            260                 265                     270

Thr Ser Lys Gly Glu Lys Ile Ala Met Leu Met Ala Ala Pro Gly Gln
        275                 280                     285

Val Ile Arg Ala Lys Thr Thr Arg Val Thr Pro Arg Pro Ala Gly Leu
    290                 295                     300

Trp Gln Arg Pro Val
305

( 2 ) INFORMATION FOR SEQ ID NO:3:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

TCGCATGCGC CAACGCCGCT GCTTGACCAC GC    32

( 2 ) INFORMATION FOR SEQ ID NO:4:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

GACGTAGAGC CGCTTCAGGT AGCCCCGGCG    30

( 2 ) INFORMATION FOR SEQ ID NO:5:

( i ) SEQUENCE CHARACTERISTICS:
    ( A ) LENGTH: 33 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:5:

```
GACGTAGAGC  CGCTCCGTAG  CCGTCGGGTC  GAC           33
```

( 2 ) INFORMATION FOR SEQ ID NO:6:

( i ) SEQUENCE CHARACTERISTICS:
    ( A ) LENGTH: 177 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:6:

```
ATGGCTTCCT  CAGTTCTTTC  CTCTGCAGCA  GTTGCCACCC  GCAGCAATGT  TGCTCAAGCT      60
AACATGGTGG  CGCCTTTCAC  TGGCCTTAAG  TCAGCTGCCT  CATTCCCTGT  TTCAAGGAAG     120
CAAAACCTTG  ACATCACTTC  CATTGCCAGC  AACGGCGGAA  GAGTGCAATG  CATGCAG        177
```

( 2 ) INFORMATION FOR SEQ ID NO:7:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:7:

```
CCTGCAGGCA  TCCAACCATG  GCGTAATCAT  GGTCAT        36
```

( 2 ) INFORMATION FOR SEQ ID NO:8:

( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:8:

```
GATCCTCTAG  AGTCGACCTG  CAGCTCGAGA    30
```

( 2 ) INFORMATION FOR SEQ ID NO:9:

( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:9:

```
AGCTTCTCGA  GCTGCAGGTC  GACTCTAGAG    30
```

ENHANCED CAROTENOID ACCUMULATION IN STORAGE ORGANS OF GENETICALLY ENGINEERED PLANTS

CROSS-REFERENCE TO RELATED APPLICATIONS

This is a continuation-in-part of application Ser. No. 07/805,061, filed Dec. 9, 1991, now abandoned, which is a continuation-in-part of application Ser. No. 07/785,569, filed Oct. 30, 1991 as a continuation-in-part, now abandoned, and a CIP of Ser. No. 07/785,568, filed Oct. 30, 1991 as a continuation-in-part, now abandoned, and a CIP of Ser. No. 07/785,566, filed Oct. 30, 1991 as a continuation-in-part, now abandoned and a CIP of Ser. No. 07/662,921, filed Feb. 28, 1991, now abandoned. This application is a CIP of Ser. No. 08/093,577, now U.S. Pat. No. 5,545,016 filed Jul. 19, 1993 as a continuation of Ser. No. 785,569, Oct. 30, 1991, abandoned; and a CIP of Ser. No. 08/096,043, now U.S. Pat. No. 5,530,189, filed Jul. 22, 1993 as a continuation of Ser. No. 785,568, Oct. 30, 1991, abandoned and a CIP of Ser. No. 08/095,726, now U.S. Pat. No. 5,530,188 filed Jul. 21, 1993 as a continuation of Ser. No. 785,566, Oct. 30, 1991, abandoned, and a CIP of Ser. No. 08/096,623 filed Jul. 22, 1993 as a continuation of Ser. No. 805,061, Dec. 9, 1991; which is a continuation-in-part of application Ser. No. 07/562,674, filed Aug. 3, 1990, now abandoned, which is a continuation-in-part of application Ser. No. 07/562,551, filed May 18, 1990, now abandoned, which is a continuation-in-part of application Ser. No. 07/487,613, filed Mar. 2, 1990, now abandoned, whose disclosures are incorporated by reference.

DESCRIPTION

1. Technical Field

The present invention relates to carotenoid biosynthesis. More specifically, this invention relates to the expression of a non-higher plant gene encoding the enzyme phytoene synthase that catalyzes the formation of the colorless carotenoid phytoene in a preselected plant storage organ such as a root, seed, fruit or tuber, leading to enhanced accumulation of one or more naturally produced colored carotenoids in that plant storage organ.

2. Background Art

Carotenoids are 40-carbon ($C_{40}$) terpenoids consisting generally of eight isoprene ($C_5$) units joined together. Linking of the units is reversed at the center of the molecule. Trivial names and abbreviations will be used throughout this disclosure, with IUPAC-recommended semisystematic names usually being given in parentheses after first mention of a trivial name.

Carotenoids are pigments with a variety of applications. Carotenoid hydrocarbons are referred to as carotenes, whereas oxygenated derivatives are referred to as xanthophylls.

The carotenoids, and particularly alpha- and beta-carotene, beta-apo-8'-carotenal (apocarotenal) and 4,4'-diketo-beta-carotene (canthaxanthin), are widely used as food coloring agents, and many carotenoids exhibit provitamin A activity. See, *Carotenoids as Colorants and Vitamin A Precursors,* J. C. Bauernfeind, ed., Chapter 2 "Carotenoids as Food Color", H. Klaui and J. C. Bauernfeind, Academic Press, New York (1981) pp. 48-317.

Phytoene (7,8,11,12,7',8',11',12'-ψ octahydro-ψ, ψ-carotene) is the first carotenoid in the carotenoid biosynthesis pathway and is produced by the dimerization of a 20-carbon atom precursor, geranylgeranyl pyrophosphate (GGPP). Phytoene has useful applications in treating skin disorders (U.S. Pat. No. 4,642,318). Phytoene is itself colorless, but is a precursor for colored carotenoids.

In some organisms, the red carotenoid lycopene (ψ,ψ-carotene) is the next carotenoid produced in the pathway. Lycopene imparts the characteristic red color to ripe tomatoes. Lycopene has utility as a food colorant and an intermediate in the biosynthesis of other carotenoids in some bacteria, fungi and green plants.

Carotenoid-specific genes that can be used for synthesis of lycopene from the ubiquitous precursor farnesyl pyrophosphate include those for the enzymes GGPP synthase, phytoene synthase, as well as phytoene dehydrogenase (desaturase) enzymes, which remove a total of four moles of hydrogen from phytoene in forming lycopene.

Interestingly, differing organisms dehydrogenate phytoene in different manners. Thus, some strains of *Rhodobacter sphaeroides* contain an enzyme that removes three moles of hydrogen in one step to form neurosporene from which another mole of hydrogen is removed to form lycopene. In *Erwinia herbicola,* a single enzyme removes all four moles of hydrogen to convert phytoene to lycopene. In higher plants, the dehydrogenation reaction appears to generally require four separate steps, with three isolable intermediates being formed at each step. Thus, phytoene forms phytofluene, that forms zeta-carotene, that forms neurosporene that then forms lycopene.

Beta-carotene (β,β-carotene) is produced from lycopene in the carotenoid biosynthesis pathway by cyclizations at both termini. It is also synthesized by a number of bacteria, fungi, and green plants. Beta-carotene has utility as a colorant for margarine and butter, as a source for synthetic and in vivo vitamin A production, and has recently been implicated as having preventative effects against certain kinds of cancers.

For example, prospective and retrospective epidemiologic studies have shown that low levels of serum or plasma beta-carotene are associated with the subsequent development of lung cancer. Because retinol (vitamin A) is not similarly related to lung cancer risk, beta-carotene appears to have a protective effect without its conversion to vitamin A. Ziegler, *Amer. Instit. Nutr.,* publication 022/3166/89, 116 (1989).

Beta-carotene is produced by the cyclization of unsaturated carotenoids in a procedure not yet well understood. Bramley et al., *Current Topics in Cellular Regulation,* 29:291, 297 (1988). Because only mutants that accumulated lycopene but not gamma-carotene (another potential precursor) have been found, it is believed that in both plants and microorganisms a single cyclase is responsible for conversion of lycopene to beta-carotene. Generally, the enzymes involved in this cyclization have been found as integral membrane proteins.

Current methods for commercial production of beta-carotene include isolation from carrots, chemical synthesis [Isler et al., U.S. Pat. No. 2,917,539 (1959)] and microbial production by *Choanephora trispora* [Zajic, U.S. Pat. Nos. 2,959,521 (1960) and 3,128,236 (1964)].

Beta-carotene is doubly hydroxylated in some plants and bacteria to form zeaxanthin (β,β-carotene-3,3'-diol), a yellow pigment that is used as a colorant in the poultry industry. Chemical synthetic methods for zeaxanthin production are known, but are inefficient and are not commercially competitive with the existing biomass sources. Such sources include corn grain, corn gluten meal and marigold petals.

The levels of zeaxanthin in corn kernels average about 0.001 percent (dry weight) and about 0.01 percent (dry weight) in corn gluten meal These biomass sources are characterized by low and inconsistent production levels.

Zeaxanthin diglucoside is another food colorant that is made biosynthetically from zeaxanthin. This material has a yellow color similar to that of zeaxanthin.

In many plants, lycopene is a branch point in carotenoid biosynthesis. Thus, some of the plant's lycopene is made into beta-carotene and zeaxanthin, and sometimes zeaxanthin diglucoside, whereas remaining portions of lycopene are formed into alpha-carotene and lutein (3,3'-dihydroxy-α-carotene) another hydroxylated compound.

Chamovitz et al., *J. Biol. Chem.*, 268(23):17348–17353 (1993) reported that lycopene formation is the rate-liming step in carotenogenesis in cyanobacteria. Based on the similarity between the carotenogeneic pathway in cyanobacteria and plants and further experimental data, those authors hypothesized that phytoene desaturation to form lycopene is also rate-limiting in higher plants.

Carotenoids in higher plants; i.e., angiosperms, are found in plastids; i.e., chloroplasts and chromoplasts. Plastids are intracellular storage bodies that differ from vacuoles in being surrounded by a double membrane rather than a single membrane. Plastids such as chloroplasts also contain their own DNA and ribosomes, can reproduce independently and synthesize some of their own proteins. Plastids thus share several characteristics of mitochondria.

In leaves, carotenoids are usually present in the grana of chloroplasts where they provide a photoprotective function. Beta-carotene and lutein are the predominant carotenoids, with violaxanthin and neoxanthin being present in smaller amounts. Carotenoids accumulate in developing chromoplasts of flower petals, usually with the disappearance of chlorophylls. As in flower petals, carotenoids appear in fruit chromoplasts as they develop from chloroplasts. Carotenoids are also located in chromoplasts in carrot roots and potato tubers. β-Carotene is the principal pigment present in both commercial carrots and sweet potatoes, with only small amounts of xanthophylls usually being present. See, T. W. Goodwin, "Carotenoids" in *Encyclopedia of Plant Physiology*, New Series, Vol. 8, Pirson et al., eds., *Secondary Plant Products*, Chapter 5.3, Bell et al., eds, Springer-Verlag, New York (1980) pages 257–287.

At the present time only a few plants are widely used for commercial colored carotenoid production. However, the productivity of colored carotenoid synthesis in most of these plants is relatively low and the resulting carotenoids are expensively produced.

One way to increase the productive capacity of biosynthesis would be to apply recombinant DNA technology. Thus, it would be desirable to produce colored carotenoids generally and beta-carotene specifically by recombinant DNA technology. That type of production permits control over quality, quantity and selection of the most suitable and efficient producer organisms. The latter is especially important for commercial production economics and therefore availability to consumers.

An organism capable of carotenoid synthesis and a potential source of genes for such biosynthetic endeavor is *Erwinia herbicola*. *Erwinia herbicola* is a member of a genus of Gram-negative bacteria of the Enterobacteriaceae family that are facultative anaerobes.

The genus Erwinia is commonly divided into three groups. Of the three, the *herbicola* group includes species (e.g., *Erwinia herbicola*) which typically form yellow pigments that have been found to be carotenoids. These bacteria exist as saprotrophs on plant surfaces and as secondary organisms in lesions caused by many plant pathogens. They can also be found in soil, water and as opportunistic pathogens in animals, including man.

Application WO 91/13078 (published Sep. 5, 1991) teaches the use of genes from *Erwinia herbicola* for the preparation of several carotenoid molecules in several mono- and multicellular organisms. In addition, European patent application 0 393 690 A1 (published Oct. 24, 1990) reports use of DNA from another Erwinia species, *Erwinia uredovora* 20D3 (ATCC 19321), for preparing carotenoid molecules.

As is discussed in detail hereinafter, the present invention most preferably utilizes DNA from *Erwinia herbicola* EHO-10 (ATCC 39368) that encodes the enzyme phytoene synthase for preparation of carotenoid molecules in higher plant storage organs. *Erwinia herbicola* EHO-10 used herein is also referred to as *Escherichia vulneris*.

Application WO 91/13078 teaches the enhanced production of phytoene in higher plants by means of a vector containing the constitutive cauliflower mosaic virus CaMV 35S promoter and *Agrobacterium tumefaciens*-mediated DNA transfer. Transfer of the gene encoding phytoene synthase linked at its N-terminus to the transit (signal) peptide of tobacco ribulose bisphosphate carboxylase-oxygenase (RUBISCO or RBCS) was also reported as a means of transporting the enzyme into plant chloroplasts where carotenoids are generally synthesized. That application also teaches the use of *Agrobacterium tumefaciens* to transfer a gene containing the above transit peptide gene and the gene for lycopene cyclase that converts lycopene into beta-carotene into plants to obtain enhanced chloroplast levels of beta-carotene.

Although the above techniques have proven successful in providing enhanced levels of carotenoids to plants systemically and plant chloroplasts, the regenerated plants so produced were often themselves yellow or orange, showed morphological deformities, and their growth was unexpectedly retarded. Thus, a better means was desired for obtaining the enhanced yield of carotenoids, and particularly alpha- and beta-carotenes, zeaxanthin and lutein in plants. The disclosure that follows illustrates two related techniques for accomplishing that desired result.

BRIEF SUMMARY OF THE INVENTION

The present invention relates to higher plants transformed to contain a heterologous genomic DNA that encodes a non-higher plant phytoene synthase linked to a plastid transit peptide, and is under the control of a promoter than provides storage organ-enhanced expression. The result of this organ-enhanced expression of an enzyme that catalyzes synthesis of the colorless carotenoid phytoene is organ-enhanced accumulation of colored carotenoids that are downstream in the synthesis pathway for that particular plant.

One aspect is a process for providing enhanced colored native carotenoid accumulation in a preselected storage organ of a transgenic higher plant as compared to the accumulation of the colored native carotenoid in that storage organ of a non-transformed plant of the same type when both plants are grown under the same conditions. This process comprises the steps of growing the transformed plant to the maturity of the preselected storage organ. The genome of the transgenic plant contains (i) a DNA segment that encodes a chimeric polypeptide conjugate operatively linked to (ii) a promoter DNA segment that drives storage organ-enhanced expression of the chimeric polypeptide conjugate. The chimeric polypeptide conjugate has an N-terminal plastid transit peptide portion whose C-terminus is peptide-bonded to the N-terminus of a non-higher plant phytoene synthase enzyme.

Another aspect of the invention is a similar process that adds the additional step of regenerating transgenic plant tissue into the transgenic plant that is grown to the maturity of the preselected storage organ.

A still further embodiment of the invention contemplates the further step of forming transgenic plant tissue by genomically transforming tissue of a plant that accumulates a colored native carotenoid in a preselected storage organ with a recombinant DNA molecule that comprises an integrating vector operatively linked to (i) a DNA segment that encodes a chimeric polypeptide conjugate and (ii) a promoter DNA segment that drives the storage organ-enhanced expression of the chimeric polypeptide conjugate in the preselected storage organ of a plant regenerated from the plant tissue. The transformed plant tissue is then regenerated into a transgenic plant that is grown to the maturity of a preselected storage organ. The colored native carotenoid can thereafter be recovered from the mature storage organ.

The storage organ of any of the above processes is preferably a root, seed, tuber or fruit. The non-transgenic plant that is transformed in an above process is preferably a potato, tomato, carrot, melon, squash, red guava, passion fruit, mango, red papaya, avocado, cherry, tangerine, mandarin, palm, cucumber, apricot, peach and maize.

A preferred plastid transit peptide is one of the tobacco RUBISCO, petunia EPSP synthase, and pepper PSY gene transit peptides. A preferred promoter is a root- or tuber-enhanced promoter, and the preferred preselected storage organ is a root or tuber, respectively. A preferred phytoene synthase enzyme is encoded by the crt B gene of *Erwinia herbicola*.

A transgenic plant is also contemplated. That plant (a) has a genomic structural gene that encodes a chimeric polypeptide conjugate and (b) over-accumulates a colored native carotenoid in a preselected storage organ relative to the accumulation of colored native carotenoid in that storage organ in a non-transgenic plant of the same type because of a promoter that causes organ-enhanced expression of that polypeptide conjugate. The chimeric polypeptide conjugate has an N-terminal plastid transit peptide portion whose C-terminus is linked to the N-terminus of a non-higher plant phytoene synthase enzyme. Hybrids of the transgenic plant that also have the structural gene that encodes the chimeric polypeptide are also contemplated.

Exemplary transgenic plants are noted before. A transgenic carrot is particularly contemplated transgenic plant. That carrot (a) has a structural gene that encodes a chimeric polypeptide conjugate and (b) over-accumulates a colored $C_{40}$ carotene or xanthophyll in the root relative to a non-transgenic carrot of the same type. The chimeric polypeptide conjugate has an N-terminal RUBISCO transit peptide portion whose C-terminus is linked to the N-terminus of the *Erwinia herbicola* phytoene synthase enzyme.

Also contemplated is a transgenic plant seed for a before-discussed transgenic plant that is capable of germinating into a transgenic plant that accumulates a colored native carotenoid relative to a non-transgenic plant of the same strain and hybrids derived therefrom. The seed contains a genomic gene that encodes a chimeric polypeptide conjugate that has an N-terminal transit peptide linked at its C-terminus to the N-terminus of a non-higher plant phytoene synthase enzyme.

DETAILED DESCRIPTION OF THE INVENTION

A. Definition of Terms

Figure 1:
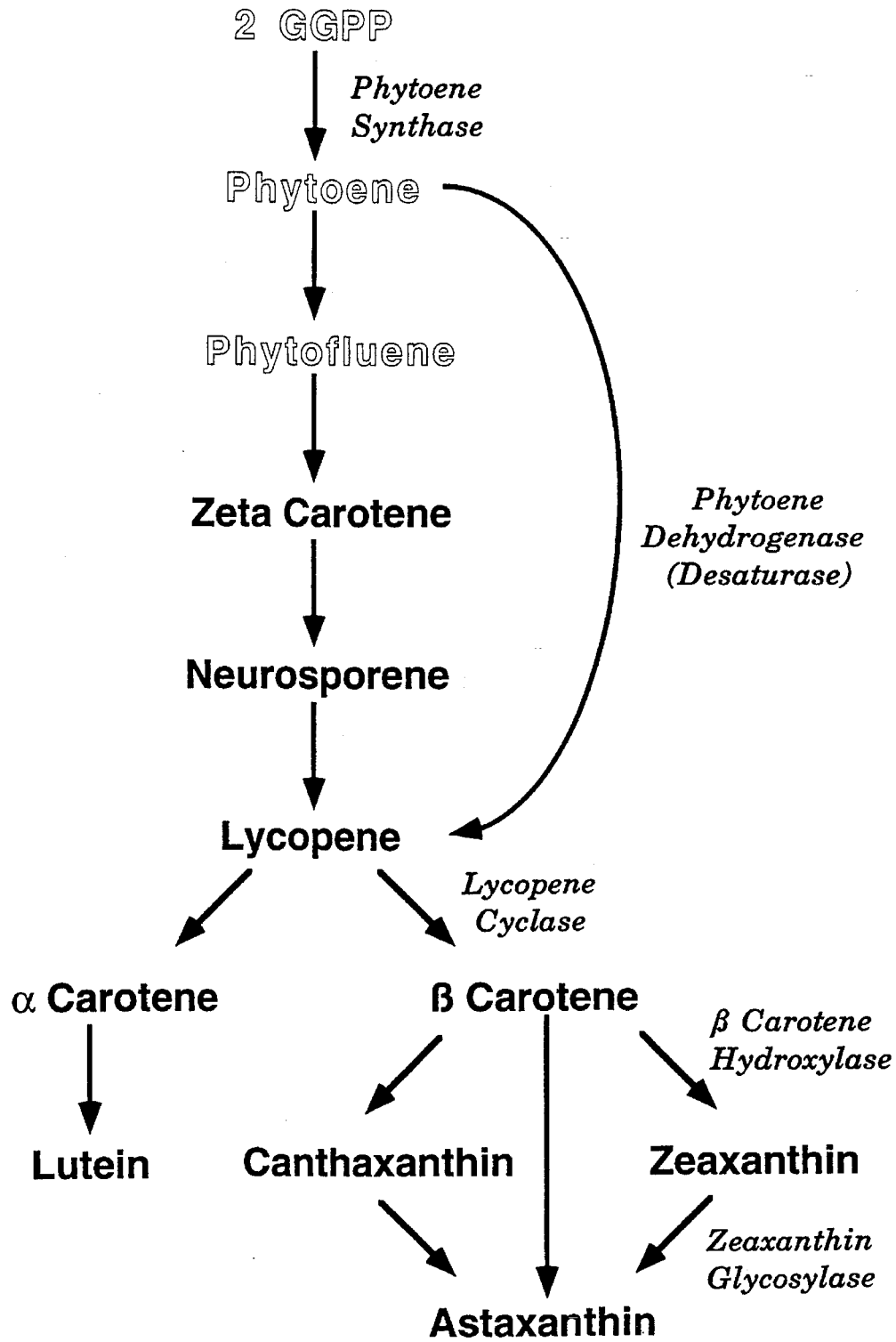
FIG. 1 is a flow diagram of a generalized carotenoid synthesis scheme in higher plants. The colorless compounds, GGPP, phytoene and phytofluene, are shown in outline letters, whereas colored carotenoids are shown in black, and enzymes are shown in black italics.

Amino Acid: All amino acid residues identified herein are in the natural L-configuration. In keeping with standard polypeptide nomenclature, *J. Biol. Chem.*, 243:3557–59 (1969), abbreviations for amino acid residues are as shown in the following Table of Correspondence:

TABLE OF CORRESPONDENCE

| SYMBOL | | |
|---|---|---|
| 1-Letter | 3-Letter | AMINO ACID |
| Y | Tyr | L-tyrosine |
| G | Gly | glycine |
| F | Phe | L-phenylalanine |
| M | Met | L-methionine |
| A | Ala | L-alanine |
| S | Ser | L-serine |
| I | Ile | L-isoleucine |
| L | Leu | L-leucine |
| T | Thr | L-threonine |
| V | Val | L-valine |
| P | Pro | L-proline |
| K | Lys | L-lysine |
| H | His | L-histidine |
| Q | Gln | L-glutamine |
| E | Glu | L-glutamic acid |
| W | Trp | L-tryptophan |
| R | Arg | L-arginine |
| D | Asp | L-aspartic acid |
| N | Asn | L-asparagine |
| C | Cys | L-cysteine |

It should be noted that all amino acid residue sequences are represented herein by formulae whose left to right orientation is in the conventional direction of amino-terminus to carboxy-terminus.

Expression: The combination of intracellular processes, including transcription and translation undergone by a structural gene to produce a polypeptide.

Expression vector: A DNA sequence that forms control elements that regulate expression of structural genes when operatively linked to those genes within a vector.

Integrated: A heterologous DNA sequence incorporated into a host chromosome is integrated.

Operatively linked or inserted: A vector DNA sequence is operatively linked to a structural gene DNA sequence if the two are covalently bonded in correct reading frame and situated so that the promoter DNA sequence influences the transcription or translation of the structural gene DNA sequence.

Promoter: A recognition site on a DNA sequence or group of DNA sequences that provide an expression control element for a gene and to which RNA polymerase specifically binds and initiates RNA synthesis (transcription) of that gene.

Recombinant DNA molecule: A hybrid DNA sequence comprising at least two nucleotide sequences not normally found together in nature.

Structural gene: A DNA sequence that is expressed as a polypeptide; i.e., an amino acid residue sequence.

Vector: A DNA molecule capable of replication in a cell and/or to which another DNA segment can be operatively linked so as to bring about replication of the attached segment. A plasmid is an exemplary vector.

B. Introduction

Constituting the most widespread group of pigments, carotenoids are present in substantially all photosynthetic organisms, where they are an essential part of the photosynthetic apparatus. Mevalonic acid, the first specific precursor of all the terpenoids is formed from acetyl-CoA via HMG-CoA (3-hydroxy-3-methylglutaryl-CoA), and is itself converted to isopentenyl pyrophosphate (IPP), the universal isoprene unit. After isomerization of IPP to dimethylallyl pyrophosphate and a series of condensation reactions adding IPP, catalyzed by prenyltransferases, geranylgeranyl pyrophosphate (GGPP) is formed by the action of the enzyme geranylgeranyl pyrophosphate synthase (GGPP synthase). This first step in carotenoid production is followed by a tail-to-tail dimerization of GGPP, catalyzed by the enzyme phytoene synthase, to form phytoene, the first $C_{40}$ carotenoid.

Each of the hydrocarbon carotenoids formed after phytoene, starting with phytofluene is colored. A generalized pathway for higher plant carotenoid biosynthesis is shown in FIG. 1.

Lycopene is made from phytoene by the catalytic action of one or more phytoene dehydrogenase (desaturase) enzymes. As shown in FIG. 1, lycopene is a branch point in higher plant carotenoid synthesis.

Cyclization of lycopene forms beta-carotene in one pathway. Lycopene cyclizes to form alpha-carotene in the other pathway of FIG. 1. Alpha- and beta-carotenes are independently cyclized to form lutein and zeaxanthin, respectively, in the two pathways. In some plants, only one terminus of lycopene cyclizes to form δ- or γ-carotene. Symmetric cyclization of γ-carotene forms α-carotene. Similarly, symmetric cyclization of δ-carotene forms ε-carotene, whereas asymmetric cyclization forms α-carotene.

A carotenoid, once formed, is the precursor for the next-made carotenoid along the biosynthetic pathway. Thus, if a carotenoid is present along with an appropriate enzyme to convert that carotenoid to the next molecule in the pathway, that conversion usually occurs.

The above product as precursor relation results in an accumulation in the plant of one or more carotenoids formed later in the biosynthetic reaction pathway relative to a small or no accumulation of earlier-formed precursor carotenoids. This relative lack of accumulation of precursor carotenoids is particularly evident where any of α- or β-carotene, lutein or zeaxanthin are the terminally-produced carotenoids in that little or no lycopene is usually observed with an observed amount of phytoene that is about ⅕ to about 1/10 that of the later-formed, colored carotenoids in mature plant parts such as fruits.

For example, one study of red bell peppers (*Capsicum annum*) reported that among the carotenoids obtained, phytoene represented about 1.7 percent as compared to capsanthin at about 34.7 percent and beta-carotene at about 11.6 percent. [Table 5, page 69 of *Carotenoids as Colorants and Vitamin A Precursors*, above.] Similarly, Table 29 at page 135 of that text that reports the carotenoid constituents of Italian Prunes shows that phytoene was present at about 1.3 percent, beta-carotene at about 18.7 percent, lutein at about 15.5 percent, and violaxanthin at about 35.0 percent, with no lycopene being reported. An examination of the data in the above text reveals that phytoene concentrations are rarely even mentioned when carotenoid analyses from various sources are discussed.

As is well known, the relative amounts of biologically produced materials are subject to several variables that here include the concentration of precursor carotenoid, the rate of enzymatic conversion to the next carotenoid and possible product feedback inhibition by which a produced carotenoid inhibits its own further reaction. Some plants may also produce a non- or poorly-functional converting enzyme so that later seemingly producible carotenoids are not produced or are produced in only relatively small amounts. Manmade inhibitors that work on late, but not early conversion enzymes can also play a role in which carotenoid is accumulated.

The plastids within storage organs of each higher plant produce characteristic colored carotenoids that accumulate to a greater extent than do other carotenoids, when that plant is grown under specified conditions. Those characteristic storage organ colored carotenoids are referred to herein as the "colored native carotenoids".

The present invention contemplates a transgenic plant and a process for using that plant. The genome of the transgenic plant contains (i) a DNA segment that encodes a chimeric polypeptide conjugate that is operatively linked to (ii) a promoter DNA segment that drives the non-photosynthetic storage organ-enhanced expression of the polypeptide conjugate. The chimeric polypeptide conjugate has an N-terminal plastid transit peptide portion whose C-terminus is linked (peptide-bonded) to the N-terminus of a non-higher plant phytoene synthase enzyme.

The process provides the enhanced accumulation of a colored native carotenoid in a preselected (predetermined) storage organ of that transgenic plant relative to the accumulation of the colored native carotenoid in a storage organ of a non-transformed plant of the same type when both plants are grown under the same conditions. In one aspect, the transgenic plant is grown to maturity of the preselected storage organ in which the enhanced amount of colored native carotenoid is expressed. In another aspect, transgenic tissue that is plant tissue transformed with a hereinafter-described vector is regenerated into a transgenic plant, and that transgenic plant is grown to the maturity of the storage organ in which carotenoid expression is enhanced. In yet another aspect, transgenic plant tissue is first formed, then regenerated into a transgenic plant that is thereafter grown to the maturity of that storage organ.

It has thus been found that enhanced plant storage organ production of a single colorless $C_{40}$ carotenoid enhances production of colored carotenoids normally produced in that storage organ; i.e., the colored native carotenoids. That colorless $C_{40}$ carotenoid, phytoene, enhances the production of the orange α- and β-carotenes and the yellow lutein and zeaxanthin, for example. Thus, rather than lycopene, as suggested by Chamovitz et al., *J. Biol. Chem.*, 268(12):17348–17353 (1993), phytoene production is the rate-limiting step in carotenogenesis in higher plants.

Enhanced production of phytoene is achieved by the provision of a transgenic plant having a genomically integrated, heterologous non-higher plant gene for the enzyme phytoene synthase. That heterologous phytoene synthase gene is expressed in a preselected (predetermined) storage organ of the higher plant into which it is transformed. It is to be understood that expression is contemplated in some storage organs that are produced during the sexual reproduction cycle of the plants such as in seeds and fruit meats, whereas in other plants the storage organ is a root such as a carrot or a tuber as in a potato or yam in which expression occurs throughout growth. In either event, the plant is grown to the maturity of the storage organ in which the enhanced amount of native colored carotenoid is expressed. It is also noted that enhanced colored native carotenoid production is not enhanced constitutively throughout the plant storage organs, but in specific, predetermined non-photosynthetic storage organs as discussed hereinafter.

A heterologous non-higher plant gene is utilized because of the phenomenon known as co-suppression by which the addition of a homologous gene causes both the native gene and transgene not to be expressed. See, for example, Fray et al., *Plant Mol. Biol.*, 22:589–692 (1993) or Finnegan et al., *Bio/Technology*, 12:883–888 (September 1994). Thus, a gene for phytoene synthase from a higher plant such as the tomato, e.g. pTOM5, or pepper plant, e.g. PSY, is not used here.

Cytoplasmic expression of a heterologous phytoene synthase gene in the preselected storage organ is not, however, sufficient for enhanced plant storage organ production of the desired, colored $C_{40}$ carotenoid(s) in that the expressed protein does not penetrate the double membrane of a plastid to any great extent, and it is in the plastid where those colored carotenoids are made. Thus, to enhance $C_{40}$ colored native carotenoid production in plant storage organ plastids, the expressed enzyme also has a plastid transit peptide fused (linked; peptide-bonded) to its N-terminal residue so that the expressed phytoene synthase enzyme can enter the plastids and form more phytoene to serve as a starting material for enhanced colored native carotenoid synthesis. The integrated heterologous phytoene synthase gene-containing DNA therefore encodes a chimeric polypeptide conjugate that includes a transit peptide linked to the non-higher plant phytoene synthase enzyme.

The contemplated enhanced production of phytoene and concomitant enhanced production of native colored $C_{40}$ carotenoids in preselected plant storage organs also requires that the chimeric polypeptide conjugate be expressed substantially only in the plant storage organ as compared to being expressed constitutively. Expression of the chimeric conjugate polypeptide is therefore driven by a DNA segment containing a storage organ-enhanced promoter. This construct provides storage organ-enhanced expression of a biologically active phytoene synthase that can catalyze phytoene production within plastids within the storage organ with little added phytoene synthesis elsewhere in the plant.

DNA segments encoding each of the promoter and chimeric polypeptide conjugate operably linked together in an integrating expression vector for plants are thus utilized herein and are discussed hereinafter.

A contemplated gene or isolated purified DNA segment that encodes phytoene synthase can be referred to as a number of base pairs at a particular location in a plasmid, or as a restriction fragment bounded by two restriction endonuclease sites, or as a restriction fragment bounded by two restriction endonuclease sites and containing a number of base pairs. A contemplated DNA such as a gene can also be defined to include a sequence of a denominated SEQ ID NO plus alleles, variants and analogs of such genes (described hereinafter) that hybridize non-randomly (i.e., specifically) with a gene shown in the SEQ ID NO or that of a phytoene synthase gene identified as a restriction fragment as discussed hereinafter under stringency conditions described hereinafter. Each contemplated gene includes a recited non-randomly (specifically) hybridizable allele, variant or analog DNA sequence, encodes phytoene synthase and also produces biologically active molecules of the encoded enzyme when suitably integrated into the genome of and expressed in an appropriate host.

Polynucleotide hybridization is a function of sequence identity (homology), G+C content of the sequence, buffer salt content, sequence length and duplex melt temperature ($T_m$) among other variables. See, Maniatis et al., *Molecular Cloning*, Cold Spring Harbor Laboratory, Cold Spring Harbor, N.Y. (1982), page 388.

With similar sequence lengths, the buffer salt concentration and temperature provide useful variables for assessing sequence identity (homology) by hybridization techniques. For example, where there is at least 90 percent homology, hybridization is carried out at 68° C. in a buffer salt such as 6XSCC diluted from 20XSSC [Maniatis et al., above, at page 447] and two sequences form a hybrid duplex (hybridize). The buffer salt utilized for final Southern blot washes can be used at a low concentration, e.g., 0.1XSSC and at a relatively high temperature, e.g. 68° C. Use of the above hybridization and washing conditions together are defined as conditions of high stringency or highly stringent conditions.

Moderately high stringency conditions can be utilized for hybridization where two sequences share at least about 80 percent homology. Here, hybridization is carried out using 6XSSC at a temperature of about 50°–55° C. A final wash salt concentration of about 1–3XSSC and at a temperature of about 60°–68° C. are used. These hybridization and washing conditions define moderately high stringency conditions.

Low stringency conditions can be utilized for hybridization where two sequences share at least 30 and more preferably about at least 40 percent homology. Here, hybridization carried out using 6XSSC at a temperature of about 40°–50° C., and a final wash buffer salt concentration of about 6XSSC used at a temperature of about 40°–60° C. effect non-random hybridization. These hybridization and washing conditions define low stringency conditions.

In living organisms, the amino acid residue sequence of a protein or polypeptide is directly related via the genetic code to the deoxyribonucleic acid (DNA) sequence of the structural gene that codes for the protein. A structural gene can be defined in terms of the amino acid residue sequence; i.e., protein or polypeptide, for which it codes.

Thus, through the well-known redundancy of the genetic code, additional DNA and corresponding RNA sequences can be prepared that encode the same amino acid residue sequences, but are sufficiently different from a before-discussed gene sequence that the two sequences do not hybridize at high stringency, but do hybridize at moderately high stringency. Thus, for example, in vitro mutagenesis as is illustrated hereinafter can be used to change a DNA sequence so that the same residue of the expressed enzyme is expressed using one or more different codons. In addition, that same technique can be used to change one amino acid residue to another where it is desired to insert or delete specific restriction endonuclease sites. This technique is also illustrated hereinafter in Example 1d where the mutation deleted a restriction site but left the amino acid sequence unchanged. Furthermore, allelic variants of a structural gene can exist in other organisms that are also useful, but form hybrid duplex molecules only at moderately high stringency.

A DNA or RNA sequence that (1) encodes a non-higher plant enzyme molecule exhibiting substantially the same biological activity as a phytoene synthase molecule expressed by a DNA sequence of SEQ ID NO:1, a herein described phytoene synthase-encoding gene, restriction fragment or DNA-containing plasmid, (2) hybridizes with a DNA sequence of that SEQ ID NO, gene, restriction fragment or plasmid at least at moderately high stringency and (3) shares at least 80 percent, and more preferably at least 90 percent, identity with a DNA sequence of that SEQ ID NO, gene, restriction fragment or plasmid DNA is defined as a DNA variant sequence.

Thus, a DNA variant or variant DNA is defined as including an RNA sequence.

Analog or analogous DNA and RNA sequences that encode the above enzyme proteins are also contemplated as part of this invention. A non-higher plant DNA and RNA sequence that (1) encodes a non-higher plant molecule exhibiting substantially the same biological activity as a phytoene synthase molecule expressed by a DNA sequence of SEQ ID NO:1, a herein-described phytoene synthase-encoding gene, restriction fragment or DNA-containing plasmid, (2) encodes an amino acid residue sequence that is at least 30 percent, and more preferably at least 40 percent, identical to that of an *Erwinia herbicola* phytoene synthase of SEQ ID NO:1, a contemplated gene, restriction fragment or plasmid, and (3) hybridizes with the structural gene of SEQ ID NO:1, gene, restriction fragment or plasmid under low stringency hybridization conditions but not at moderately high stringency are also contemplated, and is referred to herein as an "analog of" or "analogous to" a DNA or RNA sequence shown in a figure. An analog or analogous DNA sequence is thus also defined as including an RNA sequence.

C. Genes Encoding Enzymes for Phytoene Synthase Biosynthesis

As is discussed and exemplified hereinafter, a non-higher plant gene that encodes a biologically active phytoene synthase molecule other than the gene endogenous to a higher plant host; i.e., a non-higher plant heterologous phytoene synthase gene is used in the present invention. The phytoene synthase gene from *Erwinia herbicola* encoded by the so-called crtB (Eh-crtB) gene is particularly preferred, is used illustratively herein, and is discussed below.

1. Isolation of the Carotenoid Gene Cluster

The plasmid pARC376 contains an approximately 13 kb chromosomal DNA fragment isolated by Perry et al., *J. Bacteriol.*, 168:607 (1986) from the bacterium *Erwinia herbicola* EHO-10 (*Escherichia vulneris*; ATCC 39368) that when transferred into the bacterium *E. coli* causes the *E. coli* cells to produce a yellow pigment. Plasmid pARC376 was referred to by those authors as plasmid pPL376. A restriction map of the pARC376 plasmid showing appropriate restriction sites is shown in FIG. 2.

Figure 2:
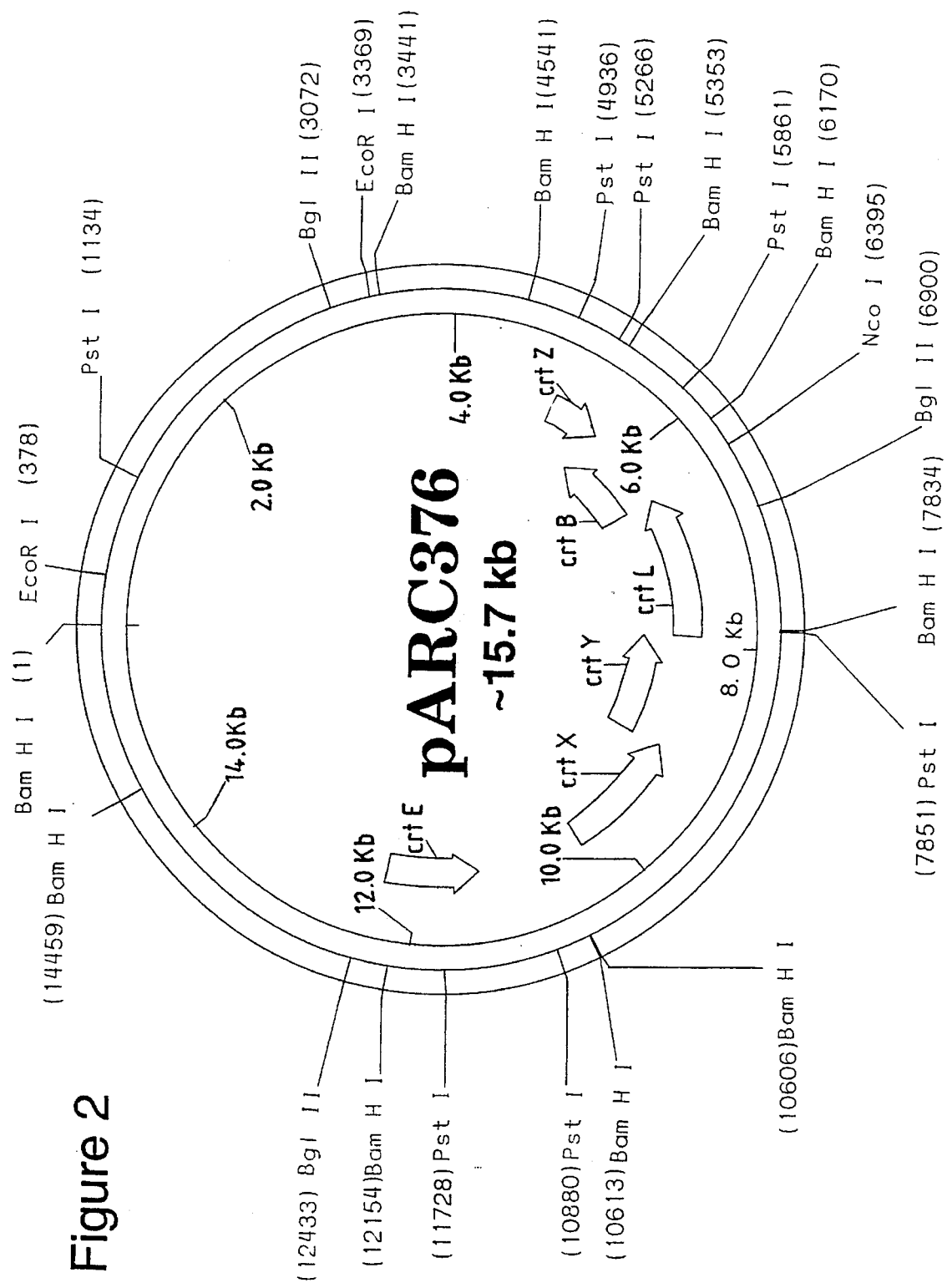
FIG. 2 schematically shows the plasmid pARC376 containing the full complement of *Erwinia herbicola* enzyme genes, represented by capital letters, required for the synthesis of carotenoids from farnesyl pyrophosphate. The direction of transcription (arrows) is uniform for all enzyme structural genes except beta-carotene hydroxylase (crt Z), which is transcribed in an opposite direction. Important restriction enzyme sites are also identified with parenthesized position numbers. The synthesis of phytoene is catalyzed by the enzymes GGPP synthase (crt E) and phytoene synthase (crt B). Genes labeled crt X, crt Y, crt I and crt Z encode the enzymes zeaxanthin glycosylase, lycopene cyclase, phytoene dehydrogenase-4H and beta-carotene hydroxylase, respectively.

The structural genes in the plasmid responsible for pigment production are present on a DNA fragment of about 7500 base pairs (bp) that is bounded by the restriction sites Pst I (at about position 4936) and Bgl II (at about position 12433) shown in FIG. 2. There are a total of six relevant genes in this approximately 7500 bp region that cause the *E. coli* cells to produce the carotenoid zeaxanthin diglucoside, which is the final product identified in the carotenoid pathway contained in plasmid pARC376 defined herein.

Although all six genes are required to be present in organisms that do not themselves produce carotenoids, and those six genes can be added to organisms that produce carotenoids, such as higher plants, it has surprisingly been found that the addition of only one gene that encodes phytoene synthase can increase the production of colored native carotenoids such as carotenes and xanthophylls in higher plant storage organs such as roots, seeds, tubers, fruits and the like. Higher plants produce farnesyl pyrophosphate and GGPP in their storage organs that are needed for phytoene preparation.

2. The Phytoene Synthase (crtB) Gene

The crtB gene of *E. herbicola* contains at least about 888 base pairs (bp), and preferably contains at least 942 bp. The gene is located between positions about 6395 and 5353 of plasmid pARC376 (FIG. 2). A useful DNA segment containing the *E. herbicoia* crtB gene (Eh-crtB) can be obtained from a number of plasmid constructs in addition to pARC376, as are discussed in published WO 91/13078 (PCT/US91/01458).

For example, plasmid pARC285 (ATCC 40756) contains the above-mentioned shorter gene within an about 1112 bp NcoI-EcoI fragment or an about 1040 bp NcoI-BamHI fragment. Plasmid pARC140N (ATCC 40759) contains the Eh-crtB gene within: an approximately 1176 bp HpaI-EcoRI fragment, an approximately 1238 bp PvuII-EcoRI fragment, as well as within a still larger fragment in the polylinker regions of that plasmid, whose length varies with the endonuclease site utilized. Another version of this gene is present in the approximately 1158 bp BglII-EcoRI fragment present in plasmid pARC145G (ATCC 40753).

Most preferably, the Eh-crtB gene used is that located on a SphI-SalI fragment of plasmid pARC1614 (about 1083 bp) that was engineered from the BglII-BamHI partial digest fragment (about 1547 bp) of pARC376 (from about position 6900 to position 5353 of FIG. 2), and is discussed hereinafter. This construct of the Eh-crtB gene has the second amino acid residue Ser changed to an Arg residue. The Eh-crtB gene used herein also had a Met at position 11 rather than the Thr of above, published WO 91/13078 that appears to have arisen spontaneously inasmuch as the sequence in WO 91/13078 agrees with the Genbank sequence deposited by others, and this region was sequenced and resequenced by the present inventors with the same result. These two genes are thus contemplated variants in that the genes function as does the native gene, encodes a protein that is more than 99 percent identical to the native gene (one or two residues changed in 309 residues) and hybridizes under stringent conditions. The SphI endonuclease cleavage site includes the ATG start codon for the gene. The DNA sequence of a construct of this gene is shown in SEQ ID NO:1.

The sequence for the Eh-crtB gene was deposited in Genbank by Armstrong et al. in 1992 and given the accession number M87280.

The sequence for a crt B gene from *Erwinia uredovora* was deposited in Genbank by Misawa et al. and given the accession number D90087. This is the same sequence published by Misawa et al. in European Application 0 393 690.

In comparing DNA sequences of *Erwinia herbicola* and *Erwinia uredovora*, the published European Application 0 393 690 reported no hybridization of DNA from *Erwinia uredovora* with DNA from *Erwinia herbicola* using highly stringent hybridization conditions. Present studies indicate a sequence identity of about 64 percent between the DNA and amino acid residue sequences of that published European application (FIG. 5) now referred to as the crtB gene and the sequences of the phytoene synthase of SEQ ID NOs:1 and 2. In spite of the about 36 percent of mismatched base pairs, and the reported non-hybridization at high stringency of the *Erwinia herbicola* and *Erwinia uredovora* DNAs, the reported *Erwinia uredovora* crtB (Eu-crtB) DNA sequence can be used here. The Eu-crtB gene and the *Erwinia herbicola* (Eh-crtB) phytoene synthase DNA used herein are DNA analogs of each other as the word "analog" is used herein.

Figure 5:
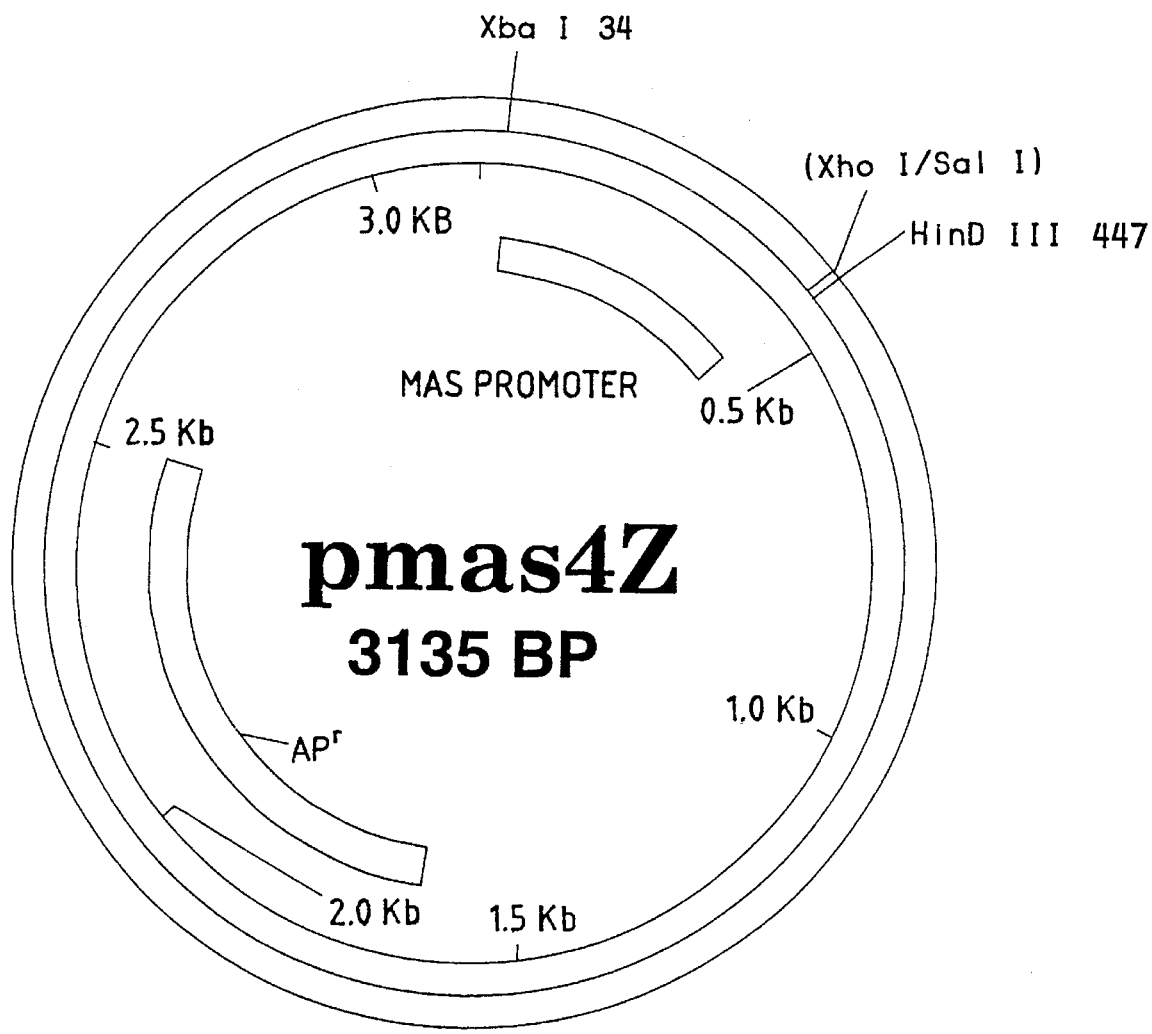
FIG. 5 schematically shows plasmid pmas4Z that contains the mas promoter (AmasPmas), and is shown as in FIG. 3.

European Application 0 393 690 misidentified the *E. uredovora* gene of FIG. 5 therein as forming prephytoene pyrophosphate (PPPP) rather than phytoene. More recently, however, one of the named inventors of that application reported that the gene of that FIG. 5 actually converts GGPP into phytoene. Sandmann et al., *FEMS Microbiol. Lett.*, 90:253–258 (1992).

Armstrong et al., *Mol. Gen. Genet.*, 216:254–268 (1989), reported work using the carotenoid-producing cluster from *Rhodobacter capsulatus*, a Gram-negative, purple, nonsulfur bacterium that is a facultative prototroph. *R. capsulatus* makes GGPP and phytoene, but does not make lycopene or cyclic carotenoids.

Armstrong et al., *Mol. Gen. Genet.*, 216:254–268 (1989) reported the gene sequences for eight members of the *R. capsulatus* crt gene cluster, including a crtB gene. Functions for five of the eight gene products were proposed, with no functions being proposed for the crtB, crtE and crtJ genes. Armstrong et al., *J. Biol. Chem*, 265(14):8329–8338 (1990) proposed that the *R. capsulatus* crtB gene converted GGPP into PPPP, whereas the crtE gene converted PPPP into phytoene, with the crtJ being required, but having no defined role. These proposals were based upon accumulation of PPPP in a crtE mutant strain and accumulation of GGPP in a crtB mutant.

Armstrong et al., *Proc. Natl., Acad. Sci., U.S.A.*, 87:9975–9979 (1990) reported the DNA sequences of *E. herbicola* crtB, crtE and crtI genes and compared the encoded proteins with proteins encoded by similarly denominated genes from *R. capsulatus*, as well as with the protein encoded by the product of the tomato pTOM5 gene. Encoded protein homologies of 33.7 percent were reported between the *R. capsulatus* crtB (Rc-crtB) and Eh-crtB gene products. Schnurr et al., *FEMS Microbiol. Lett.*, 8:157–162 (1991) reported hybridization of the *E. herbicola* crtB gene DNA with probes from *R. capsulatus* under conditions of low stringency. The *R. capsulatus* and *E. herbicola* genes are thus analogs as defined before.

Armstrong et al. deposited the sequence information for the *R. capsulatus* gene with Genbank, that deposit having accession number X52291.

More recent work by Bartley et al, *J. Biol. Chem.*, 267(8):5036–5039 (1992) reported that the *R. capsulatus* crtE gene encodes a GGPP synthase rather than a phytoene synthase. Those authors concluded that the *R. capsulatus* crtB gene is a phytoene synthase-encoding gene. More recently still, Romer et al., *Biochem. Biophys. Res. Commun.*, 196(3):1414–1421 (1993) also concluded that the *R. capsulatus* crtB gene encodes a phytoene synthase.

Recent work reported by Chamovitz et al., *FEBS Lett.*, 296(3):305–310 (1992) provided the sequence for a phytoene synthase gene denominated pys from the cyanobacterium Synechococcus sp. PCC7942. This pys gene (Syc-crtB) encodes a protein of calculated molecular weight of about 35.8 kDa. Chamovitz deposited sequence information with Genbank, that information being given accession number X63873.

Expression in *E. coli* along with a gene shown to encode GGPP synthase and a plasmid carrying the *E. uredovora* carotenoid biosynthesis genes except the crtB gene provided zeaxanthin and phytoene, and established that the pys gene encodes a phytoene synthase useful herein. Identities of 33 and 30 percents were reported in comparison of the Syc-crtB gene product to those of Eu-crtB and Re-crtB, respectively.

Another useful crtB gene sequence from the bacterium *Myxococcus xanthus* was deposited by Botella et al. with Genbank under the accession number Z21955. Comparison of the *M. xanthus* crtB gene (Mx-crtB) sequence with that of *E. herbicola* by the Clustal method provides a percent similarity of 36.5 percent.

Hoshino et al., *Appl. Environ. Microbiol.*, 59:3150–3153 (1993) published and deposited a sequence (Genbank accession No. D14604) for the phytoene synthase, crtB, gene of the bacterium *Thermus thermophilus*. Comparison of the *T. thermophilus* crtB (Tt-crtB) gene sequence with that of Eh-crtB by the Clustal method provides 32.1 percent similarity.

Viogue deposited sequence information for the phytoene synthase gene of the bacterium *Synechocystis* sp. (Syy-crtB) with Genbank under the accession number X69172. Clustal method comparison of the Syy-crtB and Eh-crtB genes shows a 26.6 percent similarity.

Yet another useful gene is the fungal phytoene synthase gene from *Neurospora crassa* (Nc-crtB) that was recently reported by Schmidhauser et al., *J. Biol. Chem.*, 269 12060–12066 (1994) and provides a corrected version of the gene sequence previously deposited with Genbank under accession number L27652. Clustal method comparison of this gene to Eh-crtB provides a similarity of 26.8 percent.

Multiple alignments by the Clustal method discussed above were performed using the Megalign application of the DNASTAR program for the Apple Macintosh computer (DNASTAR, Inc., Madison, Wis.).

Taking the above disclosures together, it is seen that any of the Eh-crtB, Eu-CrtB, Rc-crtB, Syc-crtB, Syy-crtB, Mx-crtB, Tt-crtB or Nc-crtB genes can be used as the non-higher plant gene that encodes phytoene synthase. The Eh-crtB gene is preferred and used illustratively here. Each of these genes is considered an analog of the other, whereas the Eh-crtB gene having an Arg in place of Ser and the gene of the Genbank listing are variants, with the gene having the Arg/Ser change and the Met for Thr replacement being an allelic variant of the Eh-crtB gene of the Genbank sequence.

Further analogous DNA molecules that encode phytoene synthase can be obtained from other non-higher plant organisms using hybridization and functionality selection criteria discussed herein, and in the above-cited literature. For example, a bacteria, fungus or alga that is known or can be shown to produce phytoene or a later carotenoid such as beta-carotene is utilized as a DNA source. The total DNA of the selected organism is obtained and a genomic library is constructed in a λ phage such as λgt11 using the protocols discussed in Maniatis et al., *Molecular Cloning, Cold Spring Harbor Laboratory*, Cold Spring Harbor, N.Y. (1982) at pages 270–294 or those of Bartley et al., *J. Biol. Chem.*, 267(8):5036–5039 (1992) used to obtain the PsyI gene.

The phage library is then screened under standard protocols using a radiolabeled, nick-translated DNA probe having a sequence of the *Erwinia herbicola* DNA of SEQ ID NO:1, one of the previously discussed restriction fragments from a deposited vector or one of the other useful crtB genes and the before-discussed low stringency hybridization conditions. Once the hybridization studies locate the appropriate structural gene, that structural gene DNA segment can be obtained, sequenced as necessary for use, engineered for expression in an appropriate recombinant molecule and shown to produce biologically active phytoene synthase as is discussed elsewhere herein.

The above techniques and protocols are well known to workers skilled in molecular biology and need not be discussed further. It is noted, however, that the above procedure can also be used to obtain a variant DNA molecule that encodes phytoene synthase inasmuch as DNA molecules that hybridize under conditions of low stringency also include those DNA molecules that hybridize under conditions of high and moderately high stringency.

That a DNA sequence of an allele, variant or analog encodes a "biologically active" enzyme or an enzyme having "substantially the same biological activity" is determined by whether the allele, variant or analog DNA sequence converts GGPP into phytoene; i.e., acts as a phytoene synthase enzyme. Thus, a DNA allele, analog or variant sequence that expresses a phytoene synthase-containing conjugate molecule that converts provided GGPP into phytoene is defined as biologically active, and as such, has biological activity as the referenced enzyme. Thus, referring to an expressed polypeptide conjugate as being a phytoene synthase enzyme indicates that the polypeptide is biologically active. Expression of biologically active phytoene synthase from a variant, allele or analog DNA sequence can be assayed by the production of phytoene as is discussed in the before-mentioned parental applications herein, or as similarly shown in Chamovitz et al., *FEBS Lett.*, 296(3):305–310 (1992).

D. Storage Organ Transit Peptide

The storage organ plastid transit peptide can be from substantially any source, and typically contains about 30 to about 80 amino acid residues. Exemplary useful peptides are disclosed in von Heijne et ai., *Eur. J. Biochem.*, 180:535–545 (1989); and Clark et al., *J. Biol. Chem.*, 264(29):17544–17550 (1989). Further plastid-specific (chloroplast) transit peptides are discussed more generally in della-Cioppa et al., *Plant Physiol.*, 84:965–968 (1987).

Exemplary transit peptides include the spinach ferrodoxin reductase, Rieske Fe-S protein, silene ferredoxin, pea heat-shock protein, Gln synthase, and brassica acyl carrier protein transit peptides. Amino acid residue sequences for these transit peptides and others are provided in von Heijne et al., above. DNA and amino acid residue sequences for additional silene transit peptides are disclosed in Weisbeek et al., above.

The pepper plant transit peptide gene adjacent to the PSY gene as reported by Romer et al., *Biochem. Biophys. Res. Commun.*, 196(3):1414–1421 (1993) can also be used fused to or operatively linked to one of the before-mentioned phytoene synthase genes to create a contemplated polypeptide conjugate that is heterologous to the transformed plant. The *Petunia hybrida* (MP4-G) transit peptide gene that encodes a 72 codon (216 bp) transit peptide of EPSP synthase as disclosed by Shah et al., *Science*, 233:478–481 (1986) can also be used.

A particularly preferred plastid transit peptide is a modified version of the ribulose bis-phosphate carboxylase-oxygenase (RUBISCO; RBSC) signal (transit) peptide of tobacco (*Nicotiana tabacum*) reported by Mazur et al., *Nucl. Acids Res.*, 13:2343–2386 (1985). The modifications in the gene used here introduced an NcoI site at the 5' terminus and a NarI site that cleaves between bases 73 and 74. Neither modification altered the amino acid residue sequence. The construction of this plastid transit peptide gene is discussed hereinafter.

The resulting plastid transit peptide gene contained 177 bp. This gene is preferably utilized as a 177 bp SalI-SphI fragment that can be ligated to the before-discussed SphI-SalI fragment containing the Eh-crtB gene. Such ligation creates a SalI-SalI gene (about 1260 bp) that encodes a heterologous (chimeric) polypeptide having an N-terminal transit peptide whose C-terminus is linked to the N-terminus of a polypeptide that exhibits phytoene synthase activity. Deposited plasmid pATC1616 (ATCC 40806) contains this particularly preferred SalI-SphI 177 bp DNA.

E. Storage Organ-Enhanced Promoters

As noted earlier, previous successes in producing enhanced colored carotenoid expression in plants via constitutive promoters such as the CaMV 35S and nos promoters have led to yellow and orange leaves, as well as to other morphological growth abnormalities in transformed plants. It was thus recognized that greater specificity of expression would be required to obtain the desired enhanced expression of colored native carotenoids in plants that otherwise appear and grow normally. One manner of achieving that desired result is to use a promoter that expresses its controlled gene in one or more preselected or predetermined non-photosynthetic plant organs.

Expression in one or more preselected storage organs with little or no expression in other organs such as roots versus leaves or stems is referred to herein as enhanced or preferential expression. An exemplary promoter that directs expression in one or more preselected organs as compared to another organ at a ratio of at least 5:1 is defined herein as an organ-enhanced promoter. Expression in substantially only one storage organ and substantially no expression in other storage organs is referred to as organ-specific expression; i.e., a ratio of expression products in a storage organ relative to another of about 100:1 or greater indicates organ specificity. Storage organ-specific promoters are thus members of the class of storage organ-enhanced promoters.

Plant storage organs that on maturity produce their own carotenoids are a particularly good choice for preselected organ-enhanced expression. Such organs contain plastids such as chromoplasts and chloroplasts that lose some or all of their chlorophyll during the natural maturation of the organ. Exemplary of such plastid-containing plant storage organs are the roots of carrots, potato tubers, and the meat of fruit such as red guava, passion fruit, mango, red papaya, tomato, avocado, cherry, tangerine, mandarin, palm, cantaloupe and watermelons and other fleshy fruits such as squash, cucumbers, mangos, apricots, peaches, as well as the seeds of maize (corn).

The CaMV 35S promoter is normally deemed to be a constitutive promoter. However, recent research has shown that a 21-bp region of the CaMV 35S promoter, when operatively linked into another, heterologous usual green tissue promoter, the rbcS-3A promoter, can cause the resulting chimeric promoter to become a root-enhanced promoter. That 21-bp sequence is disclosed in U.S. Pat. No. 5,023,179, whose disclosures are incorporated by reference. The chimeric rbcS-3A promoter containing the 21-bp insert of U.S. Pat. No. 5,023,179 is a useful root-enhanced promoter herein.

A similar root-enhanced promoter, that includes the above 21-bp segment is the −90 to +8 region of the CAMV 35S promoter itself. U.S. Pat. No. 5,110,732, whose disclosures are incorporated by reference, discloses that that truncated CaMV 35S promoter provides enhanced expression in roots and the radical of seed, a tissue destined to become a root. That promoter is also useful herein.

Another useful root-enhanced promoter is the −1616 to −1 promoter of the oil seed rape (*Brassica napus L.*) gene disclosed in PCT/GB92/00416 (WO 91/13922 published Sep. 19, 1991). *E. coli* DH5α harboring plasmid pRlambdaS4 and bacteriophage lambdaβ1 that contain this promoter were deposited at the National Collection of Industrial and Marine Bacteria, Aberdeen, GB on Mar. 8, 1990 and have accession numbers NCIMB40265 and NCIMB40266. A useful portion of this promoter can be obtained as a 1.0 kb fragment by cleavage of the plasmid with HaeIII.

The most preferred root-enhanced promoter is the mannopine synthase (mas) promoter present in plasmid pKan2 described by DiRita and Gelvin, *Mol. Gen. Genet,*, 207:233–241 (1987) that is used herein, and which use is discussed in detail hereinafter. This promoter is removable from its plasmid pKan2 as a XbaI—XbaII fragment.

The preferred mannopine synthase root-enhanced promoter is comprised of the core mannopine synthase (mas) promoter region up to position −138 and the mannopine synthase activator from −318 to −213, and is collectively referred to as AmasPmas. This promoter has been found to increase production in tobacco roots about 10- to about 100-fold compared to leaf expression levels. The constitutive CaMV 35S promoter exhibits about one-half the expression of AmasPmas in tobacco, and expresses well in leaf tissue.

One preferred root specific promoter is the about 500 bp 5' flanking sequence accompanying the hydroxyproline-rich glycopeprotein gene, HRGPnt3, expressed during lateral root initiation and reported by Keller et al., *Genes Dev.*, 3:1639–1646 (1989). Another preferred root-specific promoter is present in the about −636 to —1 5' flanking region of the tobacco root-specific gene ToRBF reported by Yamamoto et al., *Plant Cell*, 3:371–381 (1991). The cis-acting elements regulating expression were more specifically located by those authors in the region from about −636 to about −299 5' from the transcription initiation site. Yamamoto et al. reported steady state mRNA production from the ToRBF gene in roots, but not in leaves, shoot meristems or stems.

Still another useful storage organ-specific promoter are the 5' and 3' flanking regions of the fruit-ripening gene E8 of the tomato, *Lycopersicon esculentum*. These regions and their cDNA sequences are illustrated and discussed in Deikman et al., *EMBO J.*, 7(11):3315–3320 (1988) and *Plant Physiol.*, 100:2013–2017 (1992).

Three regions are located in the 2181 bp of the 5' flanking sequence of the gene and a 522 bp sequence 3' to the poly (A) addition site appeared to control expression of the E8 gene. One region from −2181 to −1088 is required for activation of E8 gene transcription in unripe fruit by ethylene and also contributes to transcription during ripening. Two further regions, −1088 to −863 and −409 to −263, are unable to confer ethylene responsiveness in unripe fruit but are sufficient for E8 gene expression during ripening.

The maize sucrose synthase-1 (Sh) promoter that in corn expresses its controlled enzyme at high levels in endosperm, at much reduced levels in roots and not in green tissues or pollen has been reported to express a chimeric reporter gene, β-glucuronidase (GUS), specifically in tobacco phloem cells that are abundant in stems and roots. Yang et al., *Proc. Natl. Acad. Sci., U.S.A.*, 87:4144–4148 (1990). This promoter is thus useful for plant organs such as fleshy fruits like melons, e.g. cantaloupe, or seeds that contain endosperm and for roots that have high levels of phloem cells.

Another exemplary tissue-specific promoter is the lectin promoter, which is specific for seed tissue. The lectin protein in soybean seeds is encoded by a single gene (Le1) that is only expressed during seed maturation and accounts for about 2 to about 5 percent of total seed mRNA. The lectin gene and seed-specific promoter have been fully characterized and used to direct seed specific expression in transgenic tobacco plants. See, e.g., Vodkin et al., *Cell*, 34:1023 (1983) and Lindstrom et al., *Developmental Genetics*, 11:160 (1990).

A particularly preferred tuber-specific expression promoter is the 5' flanking region of the potato patatin gene. Use of this promoter is described in Twell et al., *Plant Mol. Biol.*, 9:365–375 (1987). This promoter is present in an about 406 bp fragment of bacteriophage LPOTI. The LPOTI promoter has regions of over 90 percent homology with four other patatin promoters and about 95 percent homology over all 400 bases with patatin promoter PGT5. Each of these promoters is useful herein. See, also, Wenzler et al., *Plant Mol. Biol.*, 12:41–50 (1989).

Still further organ-enhanced and organ-specific promoter are disclosed in Benfey et al., *Science*, 244:174–181 (1988).

Each of the promoter sequences utilized is substantially unaffected by the amount of carotenoid (phytoene or colored product) in the cell. As used herein, the term "substantially unaffected" means that the promoter is not responsive to direct feedback control (inhibition) by the carotenoids or phytoene synthase accumulated in transformed cells or transgenic plants.

F. DNA Size

The previously described DNA segments are often noted as having a minimal length, as well as total overall lengths. That minimal length defines the length of a DNA segment having a sequence that encodes a particular protein enzyme, transit peptide or promoter. Inasmuch as the coding sequence for many contemplated phytoene synthase genes and transit peptides are known, isolated DNA segments, alleles, variants and analogs thereof can be prepared by in vitro mutagenesis, as described in the examples, that begin at the initial ATG codon for an enzyme gene and end at or just downstream of the end or stop codon for each gene. Thus, a desired restriction site can be engineered at or upstream of the initiation codon, and at or downstream of the stop codon of a phytoene synthase gene so that shorter phytoene synthase genes than many of those discussed above can be prepared, excised and isolated.

As is well known in the art, so long as the required DNA sequence is present, (including promoter, start and stop signals), additional base pairs can often be present at either end of the segment, particularly the 3' end, and that segment can still be utilized to express the protein. This, of course, presumes the absence in the segment of an operatively linked DNA sequence that represses expression, expresses a product that consumes a wanted reaction product produced by that desired protein, or otherwise interferes with the structural gene of the DNA segment.

Thus, so long as the promoter, transit peptide and phytoene synthase DNA-containing segment is free of such interfering DNA sequences, a DNA segment useful in the invention can be 2,000–15,000 base pairs in length. The maximum size of a recombinant DNA molecule, particularly an expression vector, is governed mostly by convenience and the vector size that can be accommodated by a host cell, once all of the minimal DNA sequences required for replication and expression, when desired, are present. Minimal vector sizes are well known. Such long DNA segments are not preferred, but can be used.

G. Construction of Plasmids

1. DNA Segments

DNA segments that encode the before-described enzyme protein, transit peptide and promoter can be synthesized by chemical techniques, for example, the phosphotriester method of Matteucci et al., *J. Am. Chem. Soc.*, 103:3185 (1981). Of course, by chemically synthesizing the coding sequence, any desired modifications can be made simply by substituting the appropriate bases for those encoding the native amino acid residue sequence. However, DNA segments including sequences discussed previously are preferred.

Furthermore, DNA segments containing structural genes encoding proteins can be obtained from recombinant DNA molecules (plasmid vectors) containing those genes. For instance, the plasmid type recombinant DNA molecules pARC285 and pARC140N each contain DNA sequences encoding the phytoene synthase protein, plasmid pARC145G contains DNA segments encoding both GGPP synthase and phytoene synthase enzymes. In addition, the plasmid type recombinant DNA molecules pARC146D and pATC1616 each contain a DNA sequence encoding biologically active phytoene dehydrogenase proteins, with plasmid pATC1616 also containing a gene for the RUBISCO plastid transit peptide.

A DNA segment that includes a DNA sequence encoding an organ-enhanced promoter operatively linked to DNA that encodes a plastid transit peptide whose DNA is linked to the 5' of a DNA segment that encodes phytoene synthase can be prepared by excising and operatively linking appropriate restriction fragments from the deposited plasmids or those discussed elsewhere herein using well known methods. The DNA molecules useful here that are produced in this manner typically have cohesive termini; i.e., "overhanging" single-stranded portions that extend beyond the double-stranded portion of the molecule. The presence of cohesive termini on the DNA molecules of the present invention is preferred, although molecules having blunt termini are also contemplated.

Each of the above plasmid vectors has been deposited pursuant to the Budapest Treaty with the American Type Culture Collection (ATCC), 12301 Parklawn Drive, Rockville, Md. 20852.

Information as to those deposits is shown below.

| Plasmid  | ATCC No. | Deposit Date      |
|----------|----------|-------------------|
| pARC285  | 40756    | February 26, 1990 |
| pARC140N | 40759    | February 26, 1990 |
| pARC145G | 40753    | February 26, 1990 |
| pARC146D | 40801    | May 11, 1990      |
| pATC1616 | 40806    | May 15, 1990      |
| pATC703  |          | October 27, 1994  |
| pATC923  |          | October 27, 1994  |

The above deposits were made in compliance with the Budapest Treaty requirements that the duration of the deposits should be for 30 years from the date of deposit or for five years after the last request for the deposit at the depository or for the enforceable life of a U.S. patent that matures from this application, whichever is longer. The plasmids will be replenished should they become non-replicable at the depository.

Ribonucleic acid (RNA) equivalents of the above described DNA segments are also contemplated.

2. Recombinant DNA Molecules

A recombinant DNA molecule useful herein can be produced by operatively linking a vector to an isolated DNA segment of the present invention to form a plasmid such as those discussed and deposited herein. Particularly preferred recombinant DNA molecules are discussed in detail in the examples, hereafter. Vectors capable of directing the expression of the gene are referred to herein as "expression vectors".

The expression vectors described above contain expression control elements including the promoter. The chimeric polypeptide coding genes are operatively linked to the expression vector to permit the promoter sequence to direct RNA polymerase binding and expression of the desired polypeptide coding gene. Useful in expressing the polypeptide coding gene are promoters which are inducible, viral, synthetic, constitutive as described by Poszkowski et al., *EMBO J.*, 3:2719 (1989) and Odell et al., *Nature*, 313:810 (1985), and temporally regulated, spatially regulated, and spatiotemporally regulated as given in Chua et al., *Science*, 244:174–181 (1989).

The choice of which expression vector and ultimately to which preselected organ-enhanced promoter a polypeptide coding gene is operatively linked depends directly on the functional properties desired, e.g. the location and timing of protein expression, and the host cell to be transformed. These are well known limitations inherent in the art of constructing recombinant DNA molecules. However, a vector useful in practicing the present invention integrates into the genome of the host higher plant, is capable of directing the replication, and also the expression of the chimeric polypeptide coding gene included in the DNA segment to which it is operatively linked. It is well known that the entire expression vector does not integrate into the host plant genome, but only a portion integrates. Nonetheless, the vector will be said to integrate for ease of expression.

In one preferred embodiment, a vector includes a prokaryotic replicon; i.e., a DNA sequence having the ability to direct autonomous replication and maintenance of the recombinant DNA molecule extrachromosomally in a prokaryotic host cell transformed therewith. Such replicons are well known in the art.

Those vectors that include a prokaryotic replicon can also include a prokaryotic promoter region capable of directing the expression of the phytoene synthase conjugate gene in a host cell, such as *E. coli*, transformed therewith. Promoter sequences compatible with bacterial hosts are typically provided in plasmid vectors containing one or more convenient restriction sites for insertion of a DNA segment of the present invention. Typical of such vector plasmids are pUC18, pUC19, and pBR322 available from Gibco BRL, Gaithersburg, Md., and pPL and pKK223-3 available from Pharmacia, Piscataway, N.J. These vectors are utilized in the synthesis of the DNA segments present in the integrating expression vectors.

Typical vectors useful for expression of genes in higher plants are well known in the art and include vectors derived from the tumor-inducing (Ti) plasmid of *Agrobacterium tumefaciens* described by Rogers et al., *Meth. in Enzymol.*, 153:253–277 (1987). These vectors are plant integrating vectors in that on transformation, the vectors integrate a portion of vector DNA into the genome of the host plant. For integrating vectors based on the Ti plasmid, the region integrated into the host plant chromosomes is that between the right and left borders of the Ti plasmid.

Exemplary *A. tumefaciens* vectors useful herein are plasmids pKYLX6 and pKYLX7 of Schardl et al., *Gene*, 61:1–11 (1987) and Berger et al., *Proc. Natl. Acad. Sci. U.S.A.*, 86:8402–8406 (1989). Plasmid pKYLX6 is an *E. coli* vector designed for intermediate constructs, whereas plasmid pKYLX7 is an *A. tumefaciens* vector designed for integration of cloned genes. Modified vectors pKYLX61 and pKYLX71 contained HindIII, XhoI, BamHI, PstI and SstI sites in place of the original HindIII-SstI fragment multiple cloning site region. Another useful vector herein is plasmid pBI101.2 that is available from Clontech Laboratories, Inc., Palo Alto, Calif. Plasmids pKYLX7, pKYLX71 and pB7101.2 are binary vectors that are used in *A. tumefaciens* with another vector having a vir gene.

Another plant transformation system is based on *Agrobacterium rhizogenes* that induces hairy roots rather than a tumor on transformation. Application PCT/US87/02512 (WO 88/02405 published Apr. 7, 1988) describes the use of *A. rhizogenes* strain A4 and its Ri plasmid along with *A. tumefaciens* vectors pARC8 or pARC16 to transform the cucumber *Cucumis sativas L.*, cv, Straight Eight, and form regenerated cucumber plants.

An Agrobacterium-based transformation system for melon, another member of the cucumber family of Curcurbitacrae, *Cucumis melo* L. was reported by Dong et al., *Bio./Technology*, 9:858–863 (1991). Those workers used a binary vector that utilized the constitutive CaMV 35S promoter not useful here, and found evidence of transformation via a reporter gene is substantially all tissues examined. This work nonetheless illustrates the amenability of melons to transformation via *A. tumefaciens*.

The use of retroviral expression vectors to form the recombinant DNAs of the present invention is also contemplated. As used herein, the term "retroviral expression vector" refers to a DNA molecule that includes a promoter sequence derived from the long terminal repeat (LTR) region of a retrovirus genome.

Because some of these carotenoid products can be associated with food production and coloration, the retroviral expression vector is preferably replication-incompetent in eukaryotic cells. The construction and use of retroviral vectors has been described by Verma, PCT Publication No. WO87/00551, and Cocking et al, *Science.*, 236:1259–62 (1987).

In preferred embodiments, the vector used to express the polypeptide coding gene includes a selection marker that is effective in a plant cell, preferably a drug resistance selection marker. One preferred drug resistance marker is the gene whose expression results in kanamycin resistance; i.e., the chimeric gene containing the hopaline synthase promoter, Tn5 necmycin phosphotransferase II and nopaline synthase 3' nontranslated region described by Rogers et al., in *Methods For Plant Molecular Bioloqy*, A. Weissbach and H. Weissbach, eds., Academic Press Inc., San Diego, Calif. (1988). Another preferred marker is the assayable chloramphenicol acetyltransferase (CAT) gene from the transposon Tn9.

A variety of methods has been developed to operatively link DNA to vectors via complementary cohesive termini or blunt ends. For instance, complementary homopolymer tracts can be added to the DNA segment to be inserted and to the vector DNA. The vector and DNA segment are then joined by hydrogen bonding between the complementary homopolymeric tails to form recombinant DNA molecules.

Alternatively, synthetic linkers containing one or more restriction endonuclease sites can be used to join the DNA segment to the integrating expression vector. The synthetic linkers are attached to blunt-ended DNA segments by incubating the blunt-ended DNA segments with a large excess of synthetic linker molecules in the presence of an enzyme that is able to catalyze the ligation of blunt-ended DNA molecules, such as bacteriophage T4 DNA ligase. Thus, the products of the reaction are DNA segments carrying synthetic linker sequences at their ends. These DNA segments are then cleaved with the appropriate restriction endonuclease and ligated into an integrating expression vector that has been cleaved with an enzyme that produces termini compatible with those of the synthetic linker. Synthetic linkers containing a variety of restriction endonuclease sites are commercially available from a number of sources including New England BioLabs, Beverly, Mass.

Also contemplated by the present invention are RNA equivalents of the above described recombinant DNA molecules.

3. Introducing Genes Into Higher Plants

Methods for introducing polypeptide coding genes into higher, multicelled flowering plants include Agrobacterium-mediated plant and callus transformation, protoplast transformation, gene transfer into pollen, injection into reproductive organs and injection into immature embryos. Each of these methods has distinct advantages and disadvantages. Thus, one particular method of introducing genes into a particular plant species may not necessarily be the most effective for another plant species, but it is well known which methods are useful for a particular plant species.

Agrobacterium-mediated transfer is a widely applicable system for introducing genes into plant cells because the DNA can be introduced into whole plant tissues, thereby bypassing the need for regeneration of an intact plant from a protoplast. The use of Agrobacterium-mediated expression vectors to introduce DNA into plant cells is well known in the art. See, for example, the methods described by Fraley et al., *Biotechnology*, 3:629 (1985) and Rogers et al., *Methods in Enzymology*, 153:253–277 (1987). Further, the integration of the Ti-DNA is a relatively precise process resulting in few rearrangements. The region of DNA to be transferred is defined by the border sequences, and intervening DNA is usually inserted into the plant genome as described by Spielmann et al., *Mol. Gen. Genet.*, 205:34 (1986) and Jorgensen et al., *Mol. Gen. Genet.* 207:471 (1987).

Modern Agrobacterium transformation vectors such as those discussed before are capable of replication in *E. coli* as well as Agrobacterium, allowing for convenient manipulations as described by Klee et al., in *Plant DNA Infectious Agents*, T. Hohn and J. Schell, eds., Springer-Verlag, New York (1985) pp. 179–203.

Moreover, recent technological advances in vectors for Agrobacterium-mediated gene transfer have improved the arrangement of genes and restriction sites in the vectors to facilitate construction of vectors capable of expressing various polypeptide coding genes. The vectors described by Rogers et al., *Methods in Enzymology*, 153:253 (1987), have convenient multi-linker regions flanked by a promoter and a polyadenylation site for direct expression of inserted polypeptide coding genes and are suitable for present purposes.

In those plant species where Agrobacterium-mediated transformation is efficient, it is the method of choice because of the facile and defined nature of the gene transfer. However, few monocots appear to be natural hosts for Agrobacterium, although transgenic plants have been produced in asparagus using Agrobacterium vectors as described by Bytebier et al., *Proc. Natl. Acad. Sci. U.S.A.*, 84:5345 (1987). Therefore, commercially important cereal grains such as rice, corn, and wheat must be transformed using alternative methods.

Agrobacterium-mediated transformation of leaf disks and other tissues such as callus appears to be limited to plant species that Agrobacterium naturally infects. Thus, Agrobacterium-mediated transformation is most efficient in dicotyledonous plants. However, as mentioned above, the transformation of asparagus using Agrobacterium can also be achieved.

Transformation of plant protoplasts can be achieved using methods based on calcium phosphate precipitation, polyethylene glycol treatment, electroporation, and combinations of these treatments. See, for example, Potrykus et al., *Mol. Gen. Genet.*, 199:183 (1985); Lorz et al., *Mol. Gen. Genet.*, 199:178 (1985); Fromm et al., *Nature*, 319:791 (1986); Uchimiya et al., *Mol. Gen. Genet.*, 204:204 (1986); Callis et al., *Genes and Development*, 1:1183 (1987); Marcotte et al., *Nature*, 335:454 (1988); Wang et al., *Bio/Technology*, 10:691–696 (1992); and Fennell et al., *Plant Cell Reports*, 11:567–570 (1992).

Application of these systems to different plant species depends upon the ability to regenerate that particular plant species from protoplasts. Illustrative methods for the regeneration of cereals from protoplasts are described in Fujimura et al., *Plant Tissue Culture Letters*, 2:74 (1985); Toriyama et al., *Theor Appl. Genet.*, 73:16 (1986); Yamada et al., *Plant Cell Rep.*, 85 (1986); Abdullah et al., *Biotechnology*, 4:1087 (1986).

To transform plant species that cannot be successfully regenerated from protoplasts, other ways to introduce DNA into intact cells or tissues can be utilized. For example, regeneration of cereals from immature embryos or explants can be effected as described by Vasil, *Biotechnology*, 6:397 (1988). In addition, "particle gun" or high-velocity microprojectile technology can be utilized. Using such technology, DNA is carried through the cell wall and into the cytoplasm on the surface of small metal particles as described in Klein et al., *Nature*, 327:70 (1987); Klein et al., *Proc. Natl. Acad. Sci. U.S.A.*, 85:8502 (1988); and McCabe et al., *Biotechnology*, 6:923 (1988); and Vasil et al., *Bio/Technology*, 9:667–674 (1992). The metal particles penetrate through several layers of cells and thus allow the transformation of cells within tissue explants.

Metal particles have been used to successfully transform corn cells and to produce fertile, stably transformed tobacco and soybean plants. Transformation of tissue explants eliminates the need for passage through a protoplast stage and thus speeds the production of transgenic plants.

DNA can also be introduced into plants by direct DNA transfer into pollen as described by Zhou et al., *Methods in Enzymology*, 101:433 (1983); D. Hess, *Intern Rev. Cytol.*, 107:367 (1987); Luo et al., *Plane Mol. Biol. Reporter*, 6:165 (1988). Expression of polypeptide coding genes can be obtained by injection of the DNA into reproductive organs of a plant as described by Pena et al., *Nature*, 325.:274 (1987). DNA can also be injected directly into the cells of immature embryos and the rehydration of desiccated embryos as described by Neuhaus et al., *Theor. Apl. Genet.*, 75:30 (1987); and Benbrook et al., in *Proceedings Bio Expo 1986*, Butterworth, Stoneham, Mass., pp. 27–54 (1986).

The regeneration of plants from either single plant protoplasts or various explants is well known in the art. See, for example, *Methods for Plant Molecular Biology*, A. Weissbach and H. Weissbach, eds., Academic Press, Inc., San Diego, Calif. (1988). This regeneration and growth process includes the steps of selection of transformant cells and shoots, rooting the transformant shoots and growth of the plantlets in soil.

The regeneration of plants containing the foreign gene introduced by Agrobacterium from leaf explants can be achieved as described by Horsch et al., *Science*, 227:1229–1231 (1985). In this procedure, transformants are grown in the presence of a selection agent and in a medium that induces the regeneration of shoots in the plant species being transformed as described by Fraley et al., *Proc. Natl. Acad. Sci. U.S.A.*, 80:4803 (1983). This procedure typically produces shoots within two to four weeks and these transformant shoots are then transferred to an appropriate root-inducing medium containing the selective agent and an antibiotic to prevent bacterial growth.

Transformation of callus is preferred herein for forming transformed plant shoots. Specific examples of such transformations are discussed hereinafter.

Transformant shoots that rooted in the presence of the selective agent to form plantlets are then transplanted to soil or other media to allow the production of roots. These procedures vary depending upon the particular plant species employed, such variations being well known in the art.

4. Carotenoid Recovery

A plant of the present invention containing the integrated promoter driving a gene encoding the transit peptide-phytoene synthase chimeric polypeptide is cultivated using methods well known to one skilled in the art suitable for the particular transformed higher plant. Any of the transgenic plants of the present invention can be cultivated to isolate the desired carotenoid products they contain.

After cultivation, the transgenic plant can be harvested to recover the carotenoid product. This harvesting step can consist of harvesting the entire plant, or only that part bearing the colored carotenoid-containing storage organ such as the fruit, tubers or roots of the plant. This step can either kill the plant or if only a non-essential portion of the transgenic plant such as the fruit is harvested can permit the remainder of the plant to continue to grow.

In preferred embodiments this harvesting step further comprises the steps of:

(i) homogenizing at least a colored carotenoid-containing portion of the transgenic plant to produce a plant pulp and using the carotenoid-containing pulp directly, as in dried pellets or tablets as where an animal, including human, food is contemplated; or (ii) extracting the colored carotenoid(s) from the plant pulp, preferably when dried, with an appropriate solvent such as an organic solvent or by supercritical extraction [Favati et al., *J. Food Sci.*, 53:1532 (1988) and the citations therein] to produce a carotenoid-containing liquid solution or suspension; and (iii) isolating the colored carotenoid(s) from the solution or suspension.

The colored carotenoid isolated in step (iii), above, is usually at least alpha- or beta-carotene, although other colored carotenoids produced can also be isolated and separated as is discussed hereinafter.

Where the storage organ containing the enhanced amount of colored native carotenoid such as a carrot root is to be eaten itself, nothing other than a usual harvest procedure is needed. The presence of enhanced amounts of color native carotenoids provides more attractive color to the food product and can also provide enhanced storage of the food through anti-oxidant characteristics of the carotenoids.

Where the colored carotenoid is to be obtained in a purer or more concentrated form, at least an appropriate portion of the transgenic plant is homogenized to produce a plant pulp using methods well known to one skilled in the art. This homogenization can be done manually, by a machine, or by a chemical means as long as the transgenic plant portions are broken up into small pieces to produce a plant pulp. This plant pulp consists of a mixture of the colored native carotenoid of interest, residual amounts of precursors, cellular particles and cytosol contents. This pulp can be dried and compressed into pellets or tablets and eaten or otherwise used to derive the benefits, or the pulp can be subjected to extraction procedures.

A colored native carotenoid such as beta-carotene can be extracted from the plant pulp produced above to form a beta-carotene-containing solution or suspension. Such extraction processes are common and well known to one skilled in this art. For example, the extracting step can consist of soaking or immersing the plant pulp in a suitable solvent. This suitable solvent is capable of dissolving or suspending the beta-carotene present in the plant pulp to produce a beta-carotene-containing solution or suspension. Solvents useful for such an extraction process are well known to those skilled in the art and include water, several organic solvents and combinations thereof such as methanol, ethanol, isopropanol, acetone, acetonitrile, tetrahydrofuran (THF), hexane, and chloroform. A vegetable oil such as peanut, corn, soybean and similar oils can also be used for this extraction. Where expression in an oil-bearing fruit such as a palm is contemplated, the oil can itself be harvested to provide the carotenoid.

The beta-carotene is isolated from the solution or suspension produced above using methods that are well known to those skilled in the art of carotenoid isolation. These methods include, but are not limited to, purification procedures based on solubility in various liquid media, chromatographic techniques such as column chromatography and the like. Isolation of xanthophylls often requires the further step of hydrolyzing xanthophyll ester products for which an alcoholic solution of sodium hydroxide can be used.

5. Genetics

A transgenic plant formed using Agrobacterium transformation methods typically contains a single gene on one chromosome. Such transgenic plants can be referred to as being heterozygous for the added gene. However, inasmuch as use of the word "heterozygous" usually implies the presence of a complementary gene at the same locus of the second chromosome of a pair of chromosomes, and there is no such gene in a plant containing one added gene as here, it is believed that a more accurate name for such a plant is an independent segregant, because the added, exogenous non-higher plant gene segregates independently during mitosis and meiosis. A transgenic plant containing an organ-enhanced promoter driving a single structural gene that encodes a chimeric polypeptide having phytoene synthase activity and its transit peptide; i.e., an independent segregant, is a preferred transgenic plant.

More preferred is a transgenic plant that is homozygous for the added structural gene; i.e., a transgenic plant that contains two added genes, one gene at the same locus on each chromosome of a chromosome pair. A homozygous transgenic plant can be obtained by sexually mating (selfing) an independent segregant transgenic plant that contains a single added gene, germinating some of the seed produced and analyzing the resulting plants produced for enhanced phytoene synthase activity, colored carotenoid accumulation, or both, relative to a control (native, non-transgenic) or an independent segregant transgenic plant. A homozygous transgenic plant exhibits enhanced phytoene synthase activity and colored carotenoid accumulation as compared to both a native, non-transgenic plant and an independent segregant transgenic plant.

It is to be understood that two different transgenic plants can also be mated to produce offspring that contain two independently segregating added, exogenous (heterologous) genes. Selfing of appropriate progeny can produce plants that are homozygous for both added, exogenous genes that encode a chimeric polypeptide having phytoene synthase activity. Back-crossing to a parental plant and out-crossing with a non-transgenic plant are also contemplated.

A transgenic plant of this invention thus has a heterologous structural gene that encodes a chimeric plastid transit peptide-containing polypeptide having phytoene synthase activity. A preferred transgenic plant is an independent segregant for the added heterologous phytoene synthase structural gene and transit peptide gene and can transmit those genes and their activity to its progeny. A more preferred transgenic plant is homozygous for those heterologous genes, and transmits those genes to all of its offspring on sexual mating.

A contemplated transgenic plant accumulates colored native carotenoids in a greater amount than does a non-transformed plant of the same type or strain when both plants are grown under the same conditions. The enhanced accumulation can be from about 1.5- to about 20-fold, and more usually about 2- to about 10-fold, as compared to the non-transformed plant. The carotenoids formed are the native carotenoids discussed before, along with phytoene, which is usually present in a minor amount as compared to the other native carotenoids.

The phrase "same type" or "same strain" is used herein to mean a plant of the same cross as or a clone of the untransformed plant. Where alleic variations among siblings of a cross are small, as with extensively inbred plant, comparisons between siblings can be used or an average arrived at using several siblings. Otherwise, clones are preferred for the comparison.

6. Development of Commercial Hybrid Seed

Seed from a transgenic plant is grown in the field greenhouse, window sill or the like, and resulting sexually mature transgenic plants are self-pollinated to generate true breeding plants. The progeny from these plants become true breeding lines that are evaluated for colored native carotenoid accumulation, preferably in the field, under a range of environmental conditions.

The commercial value of a transgenic plant with increased colored native carotenoid accumulation is enhanced if many different hybrid combinations are available for sale. The user typically grows more than one kind of hybrid based on such differences as time to maturity, standability or other agronomic traits. Additionally, hybrids adapted to one part of a country are not necessarily adapted to another part because of differences in such traits as maturity, disease and herbicide resistance. Because of this, colored native carotenoid accumulation is preferably bred into a large number of parental lines so that many hybrid combinations can be produced.

Adding an enhanced colored native carotenoid accumulation trait to an agronomically elite line is accomplished by a variety of techniques well known to those of skill in the art. For example, parent transgenic plants that are either homozygous or contain a single independent segregatable gene that encodes a chimeric polypeptide having phytoene synthase activity and thus for enhanced colored carotenoid accumulation in a desired organ are crossed with lines having other desirable traits such as herbicide resistance to produce hybrids. Preferably, transgenic plants homozygous for enhanced colored carotenoid accumulation are used to generate hybrids.

For example, a transgenic plant homozygous for enhanced colored native carotenoid accumulation is crossed with a parent plant having other desired traits. The progeny, which are heterozygous or independently segregatable for enhanced colored carotenoid accumulation, are backcrossed with one or the other parent to obtain transgenic plants having enhanced colored native carotenoid accumulation and the other desired traits. The backcrossing of progeny with the parent may have to be repeated more than once to obtain a transgenic plant that possesses all desirable traits.

Example 1: Phytoene Synthase Production in Higher Plants a. Construction of the Plasmid

Plasmid pARC283 was first constructed in order to provide an appropriate template for the polymerase chain reaction (PCR), below. The construction of plasmid pARC283 used the approximately 1547 bp BglII to BamHI partial digest fragment of plasmid pARC376 (from about position 6900 to about position 5353 of FIG. 2). Polylinker fragments, which contain multiple unique restriction sites, were ligated to the ends of this BglII-BamHI fragment. The resulting fragment was digested with EcoRI and cloned into the EcoRI site of plasmid pBR322. The resulting plasmid was named pARC283.

The phytoene synthase structural gene of this plasmid was modified to introduce the restriction site SphI at the initiation methionine codon and a SalI restriction site at the 3' end of the gene. To accomplish these modifications, the EcoRI-EcoRI fragment was excised from plasmid pARC283. This fragment was isolated on agarose gel electrophoresis and used as the template for PCR. The following oligonucleotide probe was used to create the SphI site at the ATG start codon of the phytoene synthase gene:

5' TCG CAT GCG CCA ACG CCG CTG CTT GAC CAC GC 3'
      SphI          (SEQ ID NO:3), in which bold letters indicate changed nucleotides. This modification changed the second residue from the serine shown in SEQ ID NO:1 to an arginine, thereby creating a gene that coded for a variant of the *E. herbicola* phytoene synthase.

The introduction of a SalI site at the 3' end of the phytoene synthase gene by similar PCR techniques changed the DNA sequence as indicated below:

Original Sequence:

5' GAC GTA GAG CCG CTT CAG GTA GCC CCG GCG 3'
(SEQ ID NO:4)

New Sequence:                                    Sal I

5' GAC GTA GAG CCG CTC CGT AGC CGT CGG GTC GAC
(SEQ ID NO:5), in a which bold-faced letters in the new sequence indicate an altered base.

Although there are only 15 nucleotides of the PCR probe that hybridize exactly to the original 3' sequence, the hybridization conditions under which the PCR was performed makes this amount of hybridization sufficient for the PCR to function appropriately to introduce the alterations noted in the sequence.

The probes were resuspended in a volume of sterile water such that the final concentration of each probe was 10 pmoles/µl. The PCR reaction was conducted as described below.

The GeneAmp DNA Amplification Reagent Kit (Perkin Elmer Cetus) was used to perform the reaction. The following components were mixed in the quantity and order specified according to the manufacturers instructions.

| Component | Order of Addition | Volume | Final Concentration |
|---|---|---|---|
| Sterile Water | 1 | 43.5 µl | |
| 10 × Rxn. Buffer | 2 | 10 µl | 1 X |
| 1.25 mM dNTP Mix | 3 | 16 µl | 200 µM each |
| Primer 1 (10 pMole/µl) | 4 | 10 µl | 1 µM |
| Primer 2 (10 pMole/µl) | 5 | 10 µl | 1 µM |
| Template DNA | 6 | 10 µl | 100 ng |
| Taq Polymerase | 7 | 0.5 µl | 2.5 Units |

Mineral oil (100 µl) was layered on top of the reaction mixture, and the reaction was performed using the Perkin Elmer Cetus DNA Thermal Cycler (Perkin Elmer, Prairie Cloud, Minn.). The method consisted of 25 cycles of amplification. One cycle included the following:

(1) 1 minute denaturation at 92° C.;
(2) 2 minute template priming at 37° C.;
(3) 3 minute polymerization at 72° C.;

At the end of 25 cycles, one final 7 minute polymerization at 72° C. was carried out.

After the reaction was completed the mineral oil was removed, the reaction mixture was extracted twice with ether, and the DNA was precipitated with ethanol.

b. Cloning of the PCR Produced DNA Fragment

The DNA produced by the PCR reaction was digested with SphI and SalI. This SphI-SalI PCR generated fragment (about 1083 bp) was isolated and recovered from an agarose gel. Plasmid pUC18 (Pharmacia) was likewise digested with SphI and SalI. The SphI-SalI PCR fragment was cloned into the SphI-SalI sites of plasmid pUC18. The resulting plasmid was named pATC1611.

c. Proof of Functional Genetically Engineered Phytoene Synthase Gene

The proper functioning of the phytoene synthase gene of plasmid pATC1611 was assayed by cloning the PCR modified gene into an E. coli expression vector. This was done by first digesting plasmid pATC1611 with HindIII and Eco-RI. The resulting HindIII-Eco-RI fragment was isolated and recovered from an agarose gel, and treated with the Klenow fragment of DNA polymerase I and four deoxy-nucleotide triphosphates (dNTPs) to fill in the termini to create blunt ends.

This blunt ended fragment was then cloned into plasmid pDR540 (Pharmacia), a plasmid that contains the TAC promoter active in E. coli. Thus, plasmid pDR540 was cut with BamHI, and the Klenow fragment and four dNTPs were used to fill in the ends, as above. The now blunt ended originally HindIII-EcoRI fragment containing the phytoene synthase gene was ligated to the blunt ended BamHI-treated pDR540. This plasmid construct was cut with HindIII to provide a HindIII—HindIII fragment that contained the phytoene synthase gene and the TAC promoter. That HindIII—HindIII fragment was then ligated into the HindIII site of plasmid pARC139.

Plasmid pARC139 carries a deletion in the phytoene synthase gene. Addition of a functional copy of the phytoene synthase gene to plasmid pARC139 restores the ability of E. coli cells transformed with such a construct to produce colored carotenoids. The PCR modified phytoene synthase gene led to the production of colored carotenoids in E. coli transformed with plasmid pARC139, indicating that the modifications introduced into the gene via the PCR process did not affect the production of phytoene synthase from the modified gene.

d. Construction of Plasmid pATC1614

Plasmid pATC1611 was digested with SphI and HincII. The resulting SphI-HincII fragment was cloned into the SphI and HincII sites of plasmid pATC212 to produce plasmid pATC1614. Plasmid pATC212 contains the RUBSICO transit peptide and was constructed as follows.

(i) RUBISCO Transit Peptide

The sequence of the exemplary transit peptide DNA used herein is basically that of Mazur et al., Nucl. Acids Res., 13:2343–2386 (1985) for the ribulose bisphosphate carboxylase-oxygenase signal peptide of Nicotiana tabacum. Two changes were made to the disclosed 177 bp sequence.

In the first change, two cytidine residues were added at the 5' end to create a NcoI restriction site. The second change introduced an NarI site that cleaves between bases at positive 73 and 74. This change was a G for T replacement at position 69 and a G for A replacement at position 72, both of which changes left the encoded amino acid residue sequence unchanged. The final two residues at the 3' end were deleted to provide the natural SphI restriction site sticky end.

The synthetic transit peptide-encoding DNA also therefore contained 177 bp. The single stranded coding sequence, showing the 5' NcoI and 3' SphI sticky ends, is illustrated hereinafter as SEQ ID NO:6.

(ii) Plasmid pARC480

The DNA encoding the transit peptide was synthesized synthetically from eight fragments that were annealed together in pairs by heating at 90 degrees C. for five minutes and then slowly cooling to room temperature. Fifty picomoles of each fragment were utilized. This procedure is described at pages 138 through 140 of published WO 91/13078 (PCT/US91/01458), and need not be described herein.

The resulting 177 base pair fragment was cloned into plasmid pARC466. Plasmid pARC466 is a plasmid identical to M13mp19 except that an NcoI site has replaced the native HindIII site. This plasmid contains a polylinker region including a SmaI site that is downstream from the SphI site.

The NcoI site in plasmid pARC466 was created by replacing the originally present HindIII site using in vitro mutagenesis as discussed previously. The primer used was:

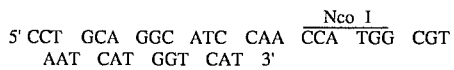

5' CCT GCA GGC ATC CAA CCA TGG CGT
AAT CAT GGT CAT 3' in which bold letters indicate changes in sequence.

Plasmid pARC466 was digested with Nco I and SphI. The 177 bp transit peptide DNA fragment ends were designed to clone into these sites. The ligation of the 177 base pair fragment into plasmid pARC466 resulted in plasmid pARC480. Plasmid pARC480 was sequenced by M13 protocol to check the sequence of the designed peptide, which sequence was found to be correct.

(iii). Plasmid DATC212

The transit peptide was moved into a plasmid that contained a plant promoter and termination sequence. pCaMVCN is a plasmid supplied by Pharmacia that contains the cauliflower mosaic virus 35S promoter and a nos polyadenylation sequence. The transit peptide was cloned next to the CaMV 35S promoter as follows:

a) Plasmid pCaMVCN was digested with the restriction enzyme SalI. Linker #1104 from New England Biolabs d(TCGACCCGGG) was digested with SalI and then ligated with the digested pCaMVCN to create plasmid pATC209.

b) Plasmid pATC209 was digested with SmaI. Plasmid pARC480 was digested with NcoI and SmaI to remove the transit peptide. The NcoI site of the transit peptide DNA was treated with the Klenow fragment of *E. coli* DNA polymerase and the four dNTPs to create a blunt end to make that fragment compatible with the SmaI site of plasmid pATC209. The double blunt-ended fragment was cloned into the SmaI-digested plasmid pATC209 to create plasmid pATC212.

e. Construction of Plasmid pATC920

The plasmid pARC1614 was digested with the restriction enzymes SphI and SalI (Bethesda Research Laboratories [BRL], Gaithersburg, Md.) according to the manufacturer's instructions. The vector pGEM4Z (Promega Corp., Madison, Wis.) was also digested with SphI and SalI and ligated with the SalI-SphI fragment (about 1083 bp) from pARC1614. (It was subsequently discovered that the SphI enzyme was inactive in both of the above reactions so that the net result was as if the DNA samples had been digested with SalI alone; i.e., the 1240 bp SalI—SalI fragment from pARC1614 was ligated into SalI digested pGEM4Z.) This new construct was designated plasmid pATC915.

Figure 3:
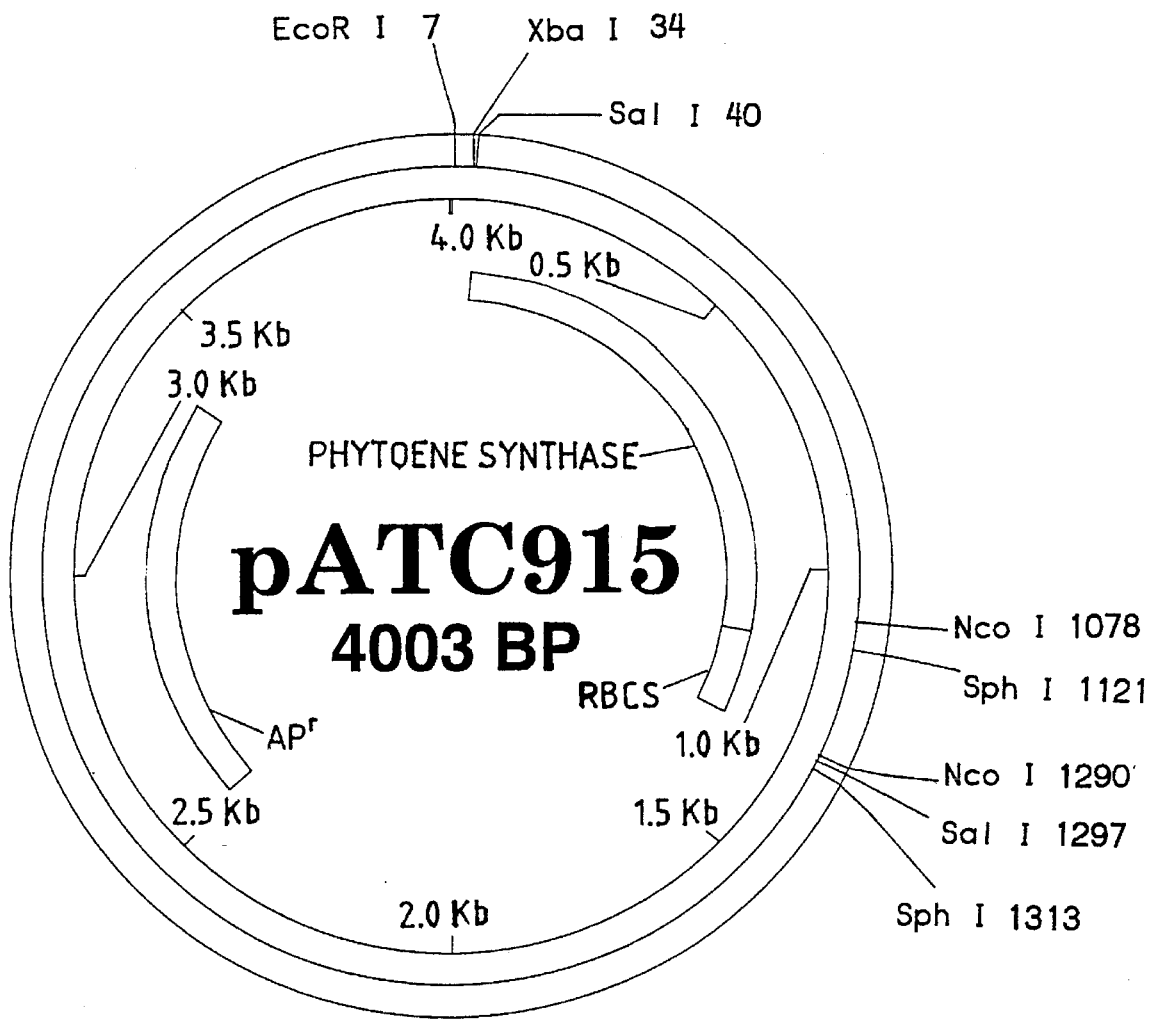
FIG. 3 schematically shows plasmid pATC915 containing genes encoding the RUBISCO (RBCS)/phytoene synthase chimeric polypeptide as well as the ampicillin resistance gene, $Ap^r$ and several important restriction enzyme sites and their position numbers.

A partial sequence of the inserted DNA was determined using the dsDNA Cycle Sequencing System (BRL) with the T7 and SP6 promoter-primers from Promega. Approximately 230 bp of sequence was determined from each end of the insert. This confirmed the identity of the clone as an *E. herbicola* phytoene synthase variant with the transit peptide from the ribulose bisphosphate carboxylase-oxygenase small subunit (RUBISCO) of *Nicotiana tabaccum* inserted immediately upstream. A map of plasmid pATC915 is shown in FIG. 3.

Subsequent manipulations of the phytoene synthase insert from plasmid pATC915 are facilitated by the additional restriction enzyme sites in the polylinker region of the vector. However, the original vector (pGEM4Z) contains an SphI site at position 56, immediately adjacent to the HindIII site. Because the recognition sequence for SphI contains 'GCATG', an additional "spurious" initiation codon is added upstream from the authentic 'ATG' of the RUBISCO transit peptide. At best this would decrease the level of expression of the desired product and, at worst, it could inhibit the expression entirely. To eliminate this problem, a modified cloning vector was constructed in which the SphI site was replaced by an XhoI site, which does not contain an 'ATG' in its recognition sequence. The vector pGEM4Z was digested with BamHI and HindIII and purified by agarose gel electrophoresis to remove the small fragment of polylinker. The large fragment was then ligated with a pair of synthetic oligonucleotides of SEQ ID NO'S:8 and 9, below, that regenerated the polylinker region with the exception of the SphI site which was replaced by an XhoI site. The resulting vector was designated pGEM4Zx.

(SEQ ID NO:8)
5'-GATCCTCTAGAGTCGACCTGCAGCTCGAGA-3'
3'-GAGATCTCAGCTGGACGTCGAGCTCTTCGA-5'
(SEQ ID NO:9)

Figure 4:
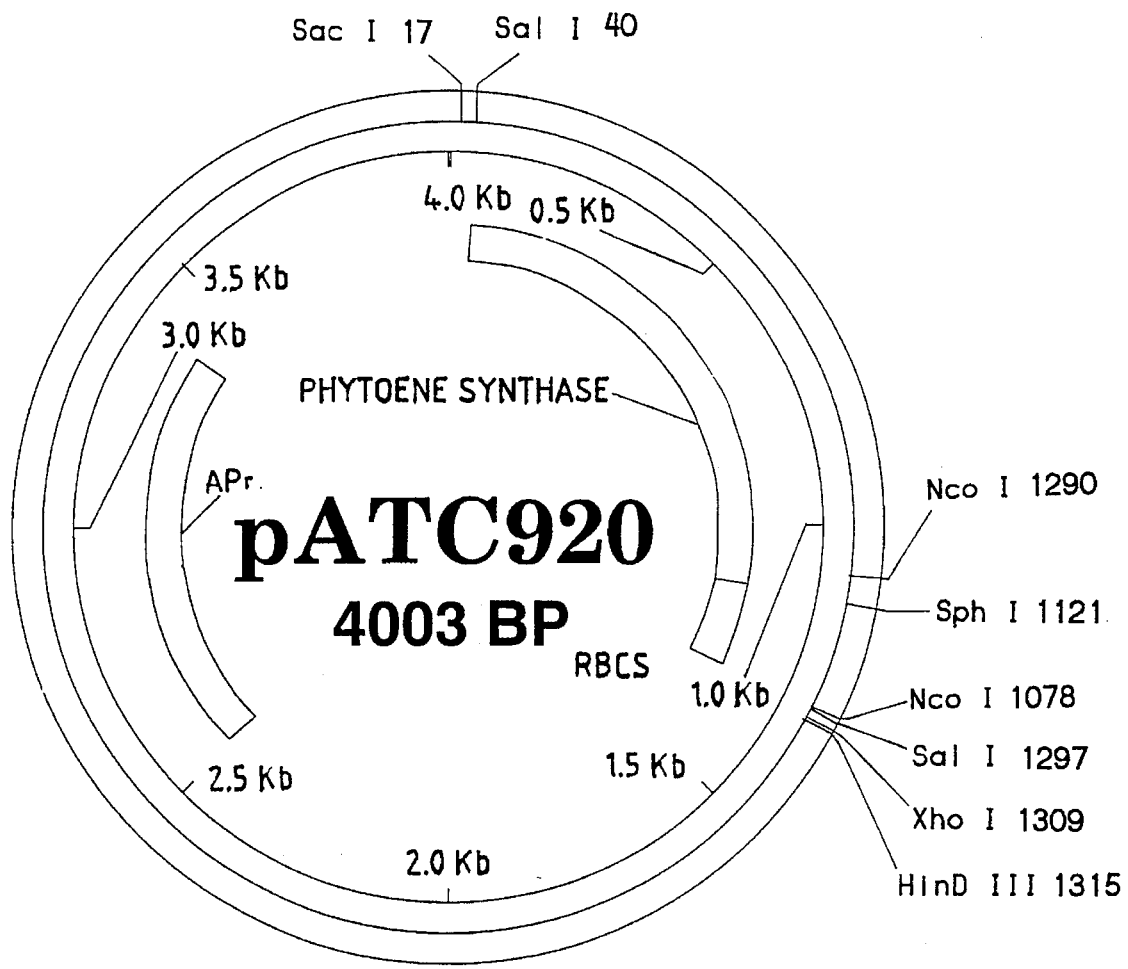
FIG. 4 schematically shows plasmid pATC920 made from pATC915, as is shown in FIG. 3.

The about 1260 SalI—SalI fragment of pARCl614 (containing the RUBISCO transit peptide and phytoene synthase gene) was ligated into SalI-digested pGEM4Zx. The new vector was designated plasmid pATC920. A map of plasmid pATC920 is shown in FIG. 4.

Example 2: Root-Enhanced Promoter

A mannopine synthase gene promoter was obtained from Dr. S. Gelvin of Purdue University. [DiRita and Gelvin, *Mol. Gen. Genet.*, 207:233–241 (1987)]. The vector of that paper (pKan2) contained the −318 AmasPmas (mas) activator-promoter construct that could be removed as an XhoI-XbaI fragment. This fragment was ligated into pGEM4Z (Promega Corp.) that had been digested with SalI and XbaI. The resulting construct was designaned plasmid pmas4Z. The sequence of the insert was determined using the dsDNA Cycle Sequencing System (BRL) with the T7 and SP6 promoter-primers from Promega. A map of plasmid pmas4Z is shown in FIG. 5.

Figure 6:
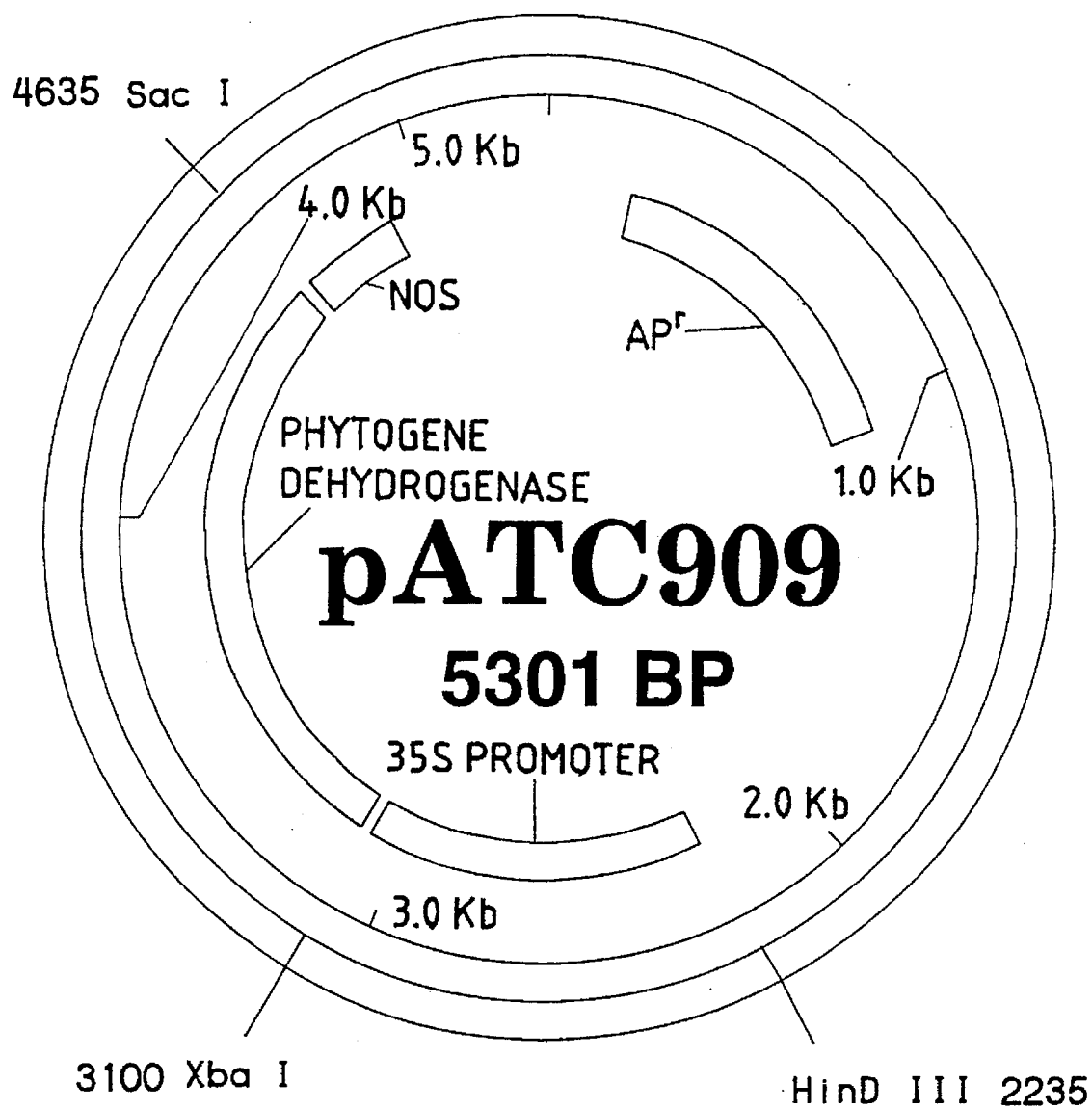
FIG. 6 schematically shows plasmid pATC909 that contains the CaMV 35S promoter operatively linked to a gene for phytoene dehydrogenase 4-H (PDH) and a nos terminator, as is shown in FIG. 3.
Figure 7:
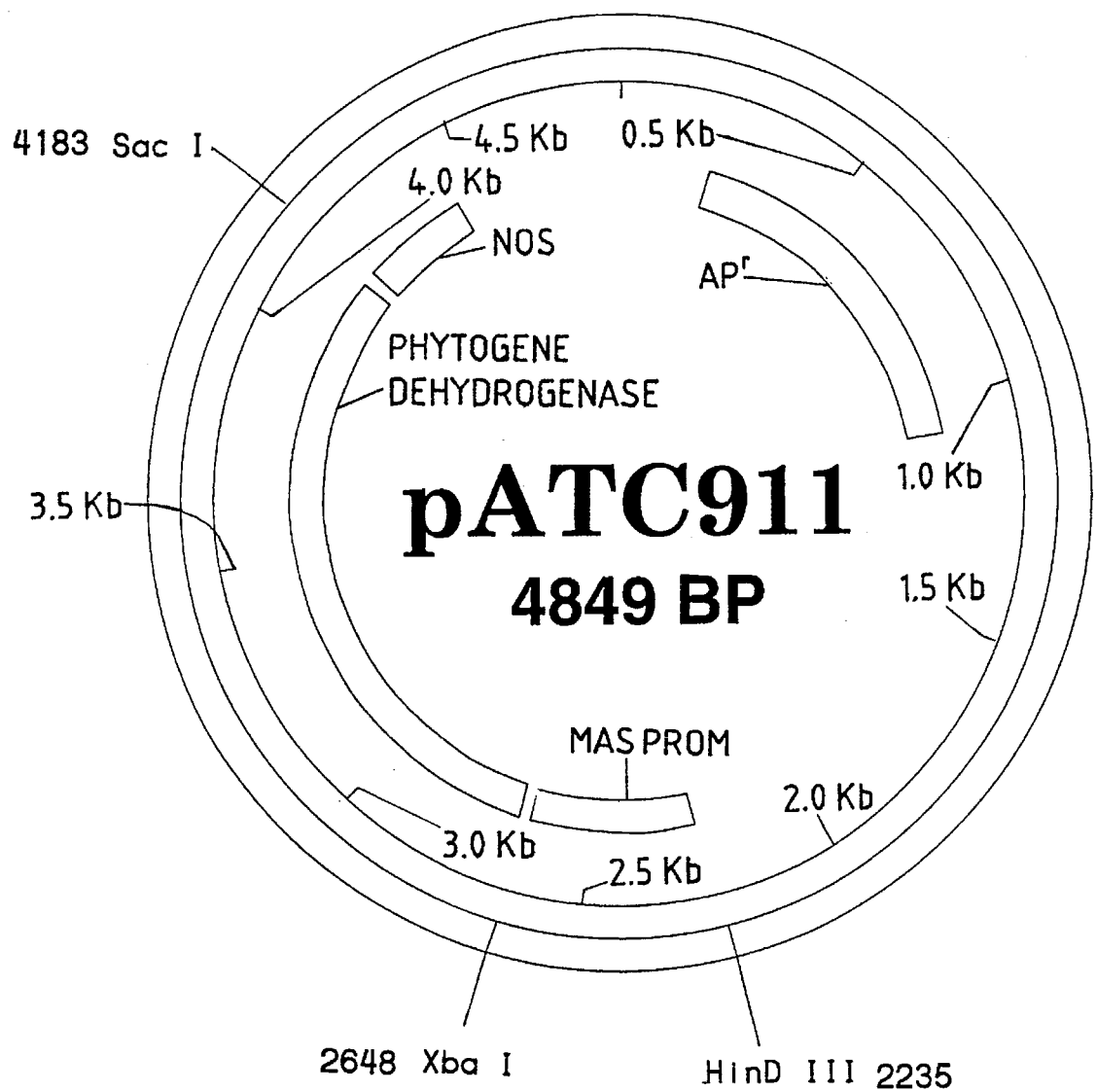
FIG. 7 schematically shows plasmid pATC911 in which the mas promoter of FIG. 5 replaced the CaMV 35S promoter of FIG. 6, as is shown in FIG. 3.

The mas promoter (MAS PROM.) was removed from pmas4Z by digestion with XbaI and HindIII, the 35S promoter was removed from pATC909 (FIG. 6) by digestion with XbaI and HindIII and the two were ligated together, yielding the plasmid pATC911 (FIG. 7). This vector contains the phytoene dehydrogenase gene from *E. herbicola* under the control of the mas promoter with a nos terminator.

Plasmid pATC909 was constructed by removing the *E. herbicola* gene for phytoene dehydrogenase (PDH) from the plasmid pARC1526 by digestion with SalI and ligating the resulting 1508 bp fragment into the XhoI site of the vector pNIU21. The construction of pNIU21 is described in Fennell and Hauptmann, *Plant Cell Reports.* 11:567–570 (1992). Plasmid pARC1526 contains the PGK promoter driving the PDH gene, followed by the PGK terminator, and was prepared for another purpose. The same PDH 1508 bp SalI—SalI fragment is present in deposited plasmid vector pARC146D (ATCC 40801) and can also be used at this step. The result is a vector (pATC909) containing the PDH gene under the control of the CaMV 35S promoter and the nos terminator. It is noted that the ligation of a SalI fragment into an XhoI site results in the regeneration of neither site.

Example 3: Root-Enhanced Promoter/Phytoene Synthase Construct-Plasmid DATC921

Figure 8:
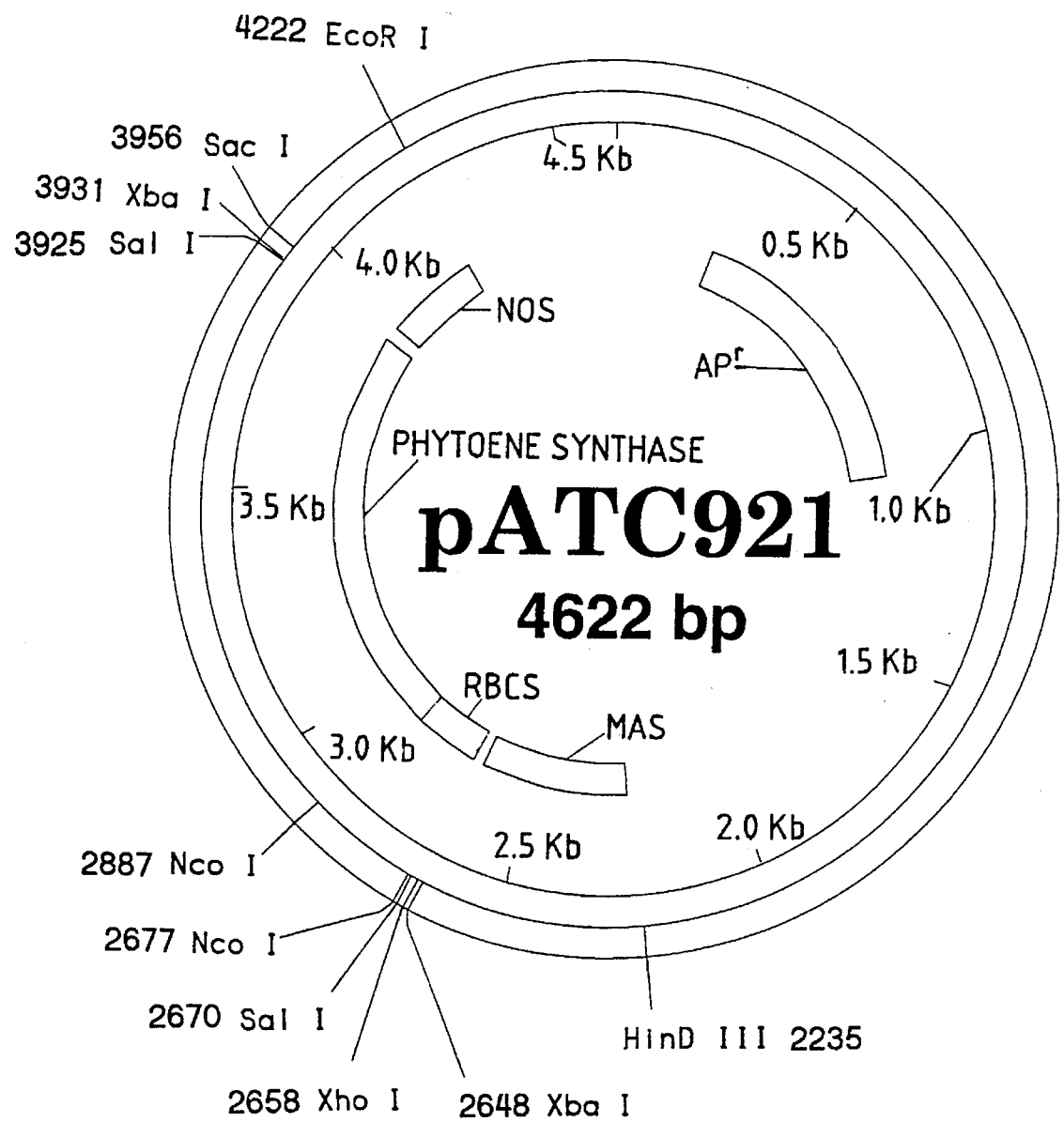
FIG. 8 schematically shows plasmid pATC921 in which the PDH gene of FIG. 6 is replaced by the RUBISCO/phytoene synthase gene of FIG. 4, as is shown in FIG. 3.

The conjugated polypeptide transit peptide/phytoene synthase gene was removed from plasmid pATC920 (FIG. 4) in a two-step process. The plasmid was digested with HindIII and the overhanging ends were filled in with the Klenow fragment of DNA polymerase and the four dNTPs to produce blunt ends. The plasmid was then digested with SacI (Promega), and the 1.3 kb gene fragment was isolated by agarose gel electrophoresis. The vector pATC911 (FIG. 7) was digested with XbaI and made blunt-ended with DNA polymerase Klenow fragment and the four dNTPs. The plasmid was then digested with SacI to remove the phytoene dehydrogenase gene. The resulting vector was purified by agarose gel electrophoresis. The transit peptide (RUBISCO)/phytoene synthase gene of plasmid pATC920 and the digested and isolated vector (pATC911) were ligated together to yield a plasmid containing a gene encoding the RUBISCO transit peptide and phytoene synthase under the control of the mas promoter (AmasPmas) with a nos terminator. This vector was designated plasmid pATC921 (FIG. 8). It is noted that after the ligation reaction, the XbaI site from plasmid pATC911 was regenerated but the Hind III site from the plasmid pATC920 insert was not regenerated. Thus, the HindIII site at position 2235 of plasmid pATC921 is unique, permitting the entire gene construct to be removed by digestion with HindIII and EcoRI.

Example 4: Binary Plasmid Construction

1. Plasmid pATC923

Figure 9:
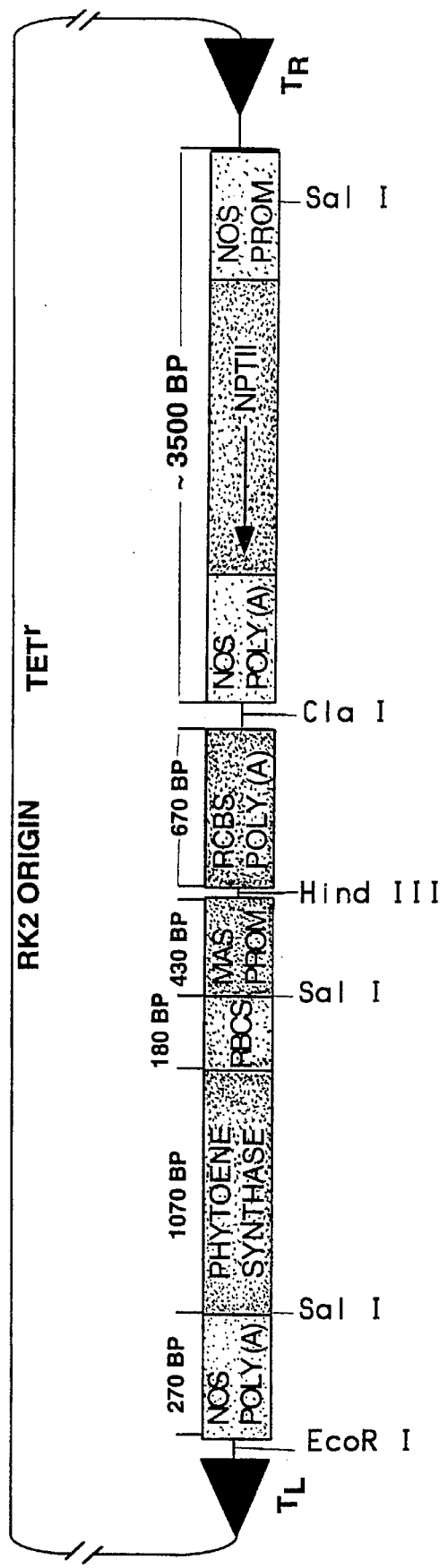
FIG. 9 schematically shows plasmic pATC923 that contains the mas-RUBISCO/phytoene synthase-nos terminator construct of FIG. 8 moved into vector pKYLX71 at the site originally occupied in that vector by the CaMV 35S promoter, as is shown in FIG. 3.

The binary vector pKYLX71 was digested with EcoRI and HindIII to remove the 35S promoter. The mas-RUBISCO/phytoene synthase-nos terminator construct was removed from pATC921 by digestion with the same two enzymes. These were ligated together to yield the vector pATC923 (FIG. 9). This is a binary vector containing the conjugate polypeptide RUBISCO transit peptide-phytoene synthase gene under the control of the mas promoter and nos terminator, and carries the genes for both kanamycin and tetracycline resistance. This vector is suitable for transformation of *Agrobacterium tumefaciens* and subsequent transformation of plant material.

2. Plasmid pATC703

Figure 10:
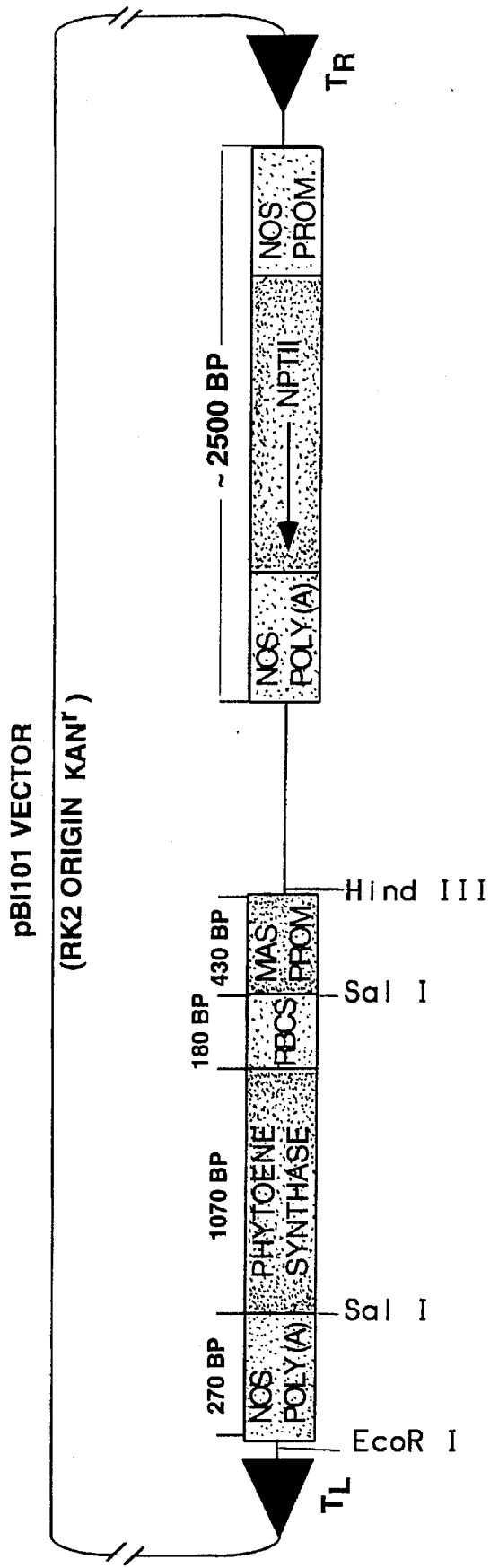
FIG. 10 schematically shows plasmid pATC703 that contains the above construct cloned into commercially available plasmid pBI101.2, as is shown in FIG. 3.

The binary vector pATC703 was constructed in a similar manner to the construction of pATC923. The mas-RUBISCO/phytoene synthase-nos terminator construct was removed from pATC921 by digestion with HindIII and EcoRI and ligated into the commercially available binary vector pBI101.2 (Clontech Laboratories, Inc., Palo Alto, Calif.) which had been digested with the same two enzymes. The result is a binary vector containing the conjugate polypeptide RUBISCO transit peptide and the phytoene synthase genes under the control of the mas promoter. This vector is designated pATC703 (FIG. 10) and carries the gene for kanamycin resistance.

Example 5: Transformation of Carrot Tissues

Danver Half Long (DHL) carrot callus tissue was transformed by *Agrobacterium tumefaciens* in separate studies using plasmids pATC923 and pATC703. Initial results using both vectors were similar. The specific results discussed below were obtained from callus transformed using pATC923 unless otherwise indicated.

a. Procedures

Carrot tissues were prepared and transformed generally as discussed in Scott et al., *Plant Mol. Biol.*, 8:265–274 (1987), with a few modifications as is described briefly as follows.

Suspension cultures were prepared from petiole, root or callus tissues in UM medium (hereinafter). Cultures were subcultured at two-week intervals, with cultures containing about $1.3 \times 10^6$ carrot plating units/Ml at the end of each time period. Transformations were carried out using 12–16 week old cultures as compared to the 8–10 week old cultures of Scott et al.

Feeder plates were prepared using 10–14 day old feeder culture (from the last subculture) of carrot cells in 0.8 percent molten agar by admixture of about 70 ml feeder cells per one liter of agar in UM or MSD media (hereinafter). The resulting admixture was thoroughly mixed and poured into 8.5 cm diameter Petri dishes. When solidified, an 8.5 cm diameter sterile Whatmann #1 filter disc was added to the top of each plate followed by a 5 cm diameter sterile "transfer disc" on top. The feeder plates so prepared were incubated for three days under continuous light at ambient room temperature.

Transfer discs were thereafter inoculated with about 0.1–0.2 ml of suspension cultures taken about two weeks after the last subculture. When the culture used is clumpy, it is first sieved through 60–80 mesh sieves. The plates are then incubated 5–7 days.

One- to two-day old *Agrobacterium tumefaciens* cultures were diluted to about $10^4$ cells/ml, and were inoculated onto the above seeded transfer discs. These transfer discs were incubated about 5–7 days or until the first visible *A. tumefaciens* growth appeared. The transfer discs were placed in selective media, UMKC or MSDKC (hereafter), and incubated for 2–4 weeks. Colonies that continued to grow at the end of that time period were transferred to fresh selective medium.

The embryogenic calli were then transferred to MSKC medium without hormones to select for regeneration. Somatic embryos developed over the next 2–3 weeks. When plantlets were about 5–7 cm long, they were transferred to sterile soil and covered to maintain humidity.

b. Media

Media used here were based upon Muroshige and Skoog (MS) basal salt mixture (Sigma Chemical Co., St. Louis, Mo.; catalogue No. M5524).

Medium MSD contained the following:

MS salts diluted per the instructions;

3% sucrose;

1 ml/L Gamburgs B5 vitamins (Sigma G1019);

2,4-dichlorophenoxyacetic acid (2,4-D) @2 mg/L; and 8 g/L Difco Agar;

pH =5.8.

UM medium contained all of the MSD ingredients plus the following:

Kinetin @0.25 mg/L;

Casein hydrolysate (enzymatic) @2 g/L; and

Glycine @2 mg/L.

KC media were the above media plus kanamycin (K) added at 100 mg/L and cefotoxime (C) added at 250 mg/L. If *A. tumefaciens* overgrowth became a problem, carbenicillin at 400–500 mg/L was also added to the selection media.

c. Results

Transformed tissues were selected by kanamycin resistance. The isolated calli ranged from dark orange to an appearance approaching that of controls. Callus pieces were further selected and subcultured based upon uniformity of color. Heterogeneous callus frequently had a bright orange color surrounded by lighter colored callus. This differential color reflects the commonly observed phenomenon in plant transformation called "position effects" that result in the insertion of genes in regions of the chromosome with differential transcriptional activity. The more active the region, the more active the transgene. As a consequence, each independent transformant expresses a gene at differing levels.

In plants regenerated from dark yellow transformants, the plantlets were yellow in color, indicating that the phytoene synthase gene was expressing at levels that would interfere with photosynthesis in the leaf tissues. In plants regenerated from light yellow transformants, the plantlets were green with bright orange tips in the shoots and roots. As the plants matured and differential gene expression commenced, the plants began to have a normal appearance and carotenoids production was enhanced in the roots.

Example 6: Window Sill Culture of Regenerates

Regenerated transgenic carrots from the above callus study (DHL-PS), regenerated control (native) carrots (DHL) and carrots regenerated from the Wisconsin high β-carotene variety, HCM, a publically available variety derived from a USDA breeding program, were grown on a window sill and all had a similar appearance with respect to growth habit and leaf appearance. Some of the transformed DHL plants exhibited a visible yellow color and some streaking. Root masses were also comparable, with a DHL control plant producing 38.6 g, DHL-PS plant producing 37.5 g and the HCM plant producing 30.75 g, based on fresh weight of root tissue. All of these regenerates exhibited the commonly found abnormally shaped roots due to damage of the tap root meristem that arises from tissue culture regeneration. These root shape abnormalities disappear in carrot plants grown from seed produced from regenerates.

Roots from all these plants were transversely sectioned at the mid-point. The control DHL root had a light green central region, whereas the transformed DHL-PS was yellow/orange throughout the cross sections. The HCM variety had a deeper overall color than did the DHL-PS root.

The color differences between the control DHL and transformed DHL-PS root evidence that root-enhanced phytoene production resulted in enhanced production of colored carotenoids. The more uniform color of the transgenic carrot root also provides an advantage to the commercial producers who favor carrot roots of uniform color.

Table 1, below, illustrates carotenoid production from the roots of the window sill-grown plants. Data are presented in percentages of dry weight, with "Fold Increase" being determined for the total of the carotenoids assayed relative to native DHL root.

TABLE 1

Carotenoid Produced in Window Sill-Regenerated Transgenic and Non-Transgenic Carrot Root

| Plant | α-Carotene | β-Carotene | Phytoene | Zeaxanthin or Lutein | Total | Fold Increase |
|---|---|---|---|---|---|---|
| DHL (Control) | 0.0203 | 0.0283 | 0.0025 | 0.0093 | 0.0604 | 1 |
| DHL-PS (Transgenic) | 0.0638 | 0.0638 | 0.0133 | 0.0115 | 0.1569 | 2.6 |
| HCM (Control) | 0.1510 | 0.1273 | 0.0123 | 0.0065 | 0.2971 | 4.9 |

As is seen from the above results, all of the carotenoids increased by enhancing the expression of phytoene synthase, and therefore phytoene. The colored carotenoids increased about 2.4-fold in the transgenic plant (DHL-PS) over the native, non-transformed plant (DHL).

Example 7: Greenhouse Culture of Regenerates

Over 200 transgenic DHL-PS carrot plants were produced in the above study. Many of those plants were transferred to greenhouse culture along with regenerated DHL plants. Table 2, below, illustrates averaged percentage values for carotenoids obtained from roots of four regenerated control DHL plants (±SD), and six individual transformant DHL-PS plants, based on dry weights. The final entry, "Fold Increase" is that of the total carotenoids assayed relative to control DHL roots. Transgenic carrot roots identified by "703-number" were transformed using plasmid pATC703, whereas those identified by "923-number" were transformed with plasmid pATC923.

TABLE 2

Percent Carotenoid Production in Transformed and Non-Transformed Carrot Roots

| Plant | α-Carotene | β-Carotene | Phytoene | Zeaxanthin or Lutein | Total | Fold Increase |
|---|---|---|---|---|---|---|
| Control | 0.0076 (0.0035) | 0.0137 (0.0027) | 0.0017 (0.0009) | 0.0024 (0.0015) | 0.0254 (0.0077) | 1 |

TABLE 2-continued

Percent Carotenoid Production in Transformed and Non-Transformed Carrot Roots

| Plant | α-Carotene | β-Carotene | Phytoene | Zeaxanthin or Lutein | Total | Fold Increase |
|---|---|---|---|---|---|---|
| Transgenic | | | | | | |
| 7103-2 | 0.0506 | 0.0674 | 0.0145 | 0.0020 | 0.1345 | 5.3 |
| 703-3 | 0.0287 | 0.0450 | 0.0086 | 0.0052 | 0.0875 | 3.4 |
| 703-4 | 0.0170 | 0.0245 | 0.0034 | 0.0030 | 0.0478 | 1.9 |
| 703-5 | 0.0132 | 0.0219 | 0.0039 | 0.0048 | 0.0437 | 1.7 |
| 923-1 | 0.0281 | 0.0338 | 0.0049 | 0.0041 | 0.0710 | 2.8 |
| 923-2 | 0.0496 | 0.0678 | 0.0114 | 0.0060 | 0.1347 | 5.3 |

The above results again illustrate the enhanced production of colored carotenoids obtained from carrot roots by transformation with an integrating vector having an organ-enhanced promoter, AmasPmas, operatively linked to agene that encodes a chimeric polypeptide conjugate having an N-terminal plastid transit peptide, RUBISCO, whose C-terminus is linked to the N-terminus of a polypeptide that exhibits phytoene synthase activity, the product of the Eh-crtB gene. Position effects on expression were also observed in these studies. Fold increases for colored carotenoids are slightly smaller than those shown for total carotenoids.

Example 8: Enhanced Colored Carotenoids Accumulation in Potato Tubers

An orange-fleshed potato originally from the Peruvian Andes (88K3.58) produces colored carotenoids such as zeaxanthin in their tuber storage organs. Potato 88K3.58, a gift of Dr. C. R. Brown of the USDA produced 0.0064 weight percent (dry weight) zeaxanthin, as well as smaller amounts of lutein and other carotenoids. Brown et al., *J. Amer. Soc. Hort. Sci.*, 118(1):145–150 (1993).

1. Plasmid pPPR001

Figure 11:
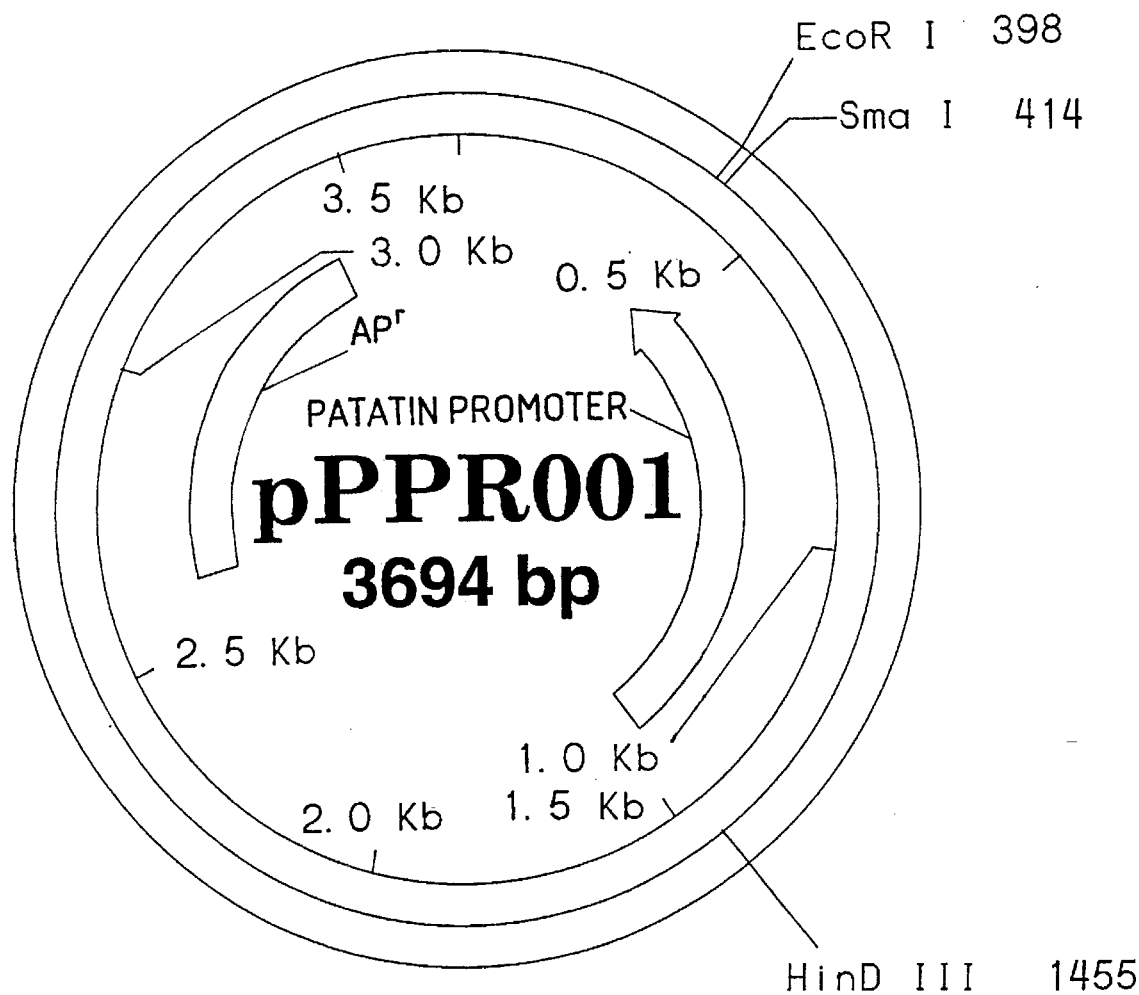
FIG. 11 schematically shows plasmid pPPR001 that contains the potato patatin promoter, as is shown in FIG. 3.

Plasmid pPPR001 contains the papatin promoter, and was constructed by and obtained from Dr. W. Belknap of the USDA, Agricultural Research Service, Western Regional Research Center, Albany, Calif. Briefly, the patatin promoter was synthesized by polymerase chain reaction (PCR) over the region of sequence corresponding to positions 1271 to 2309 of the Genbank sequence STPATG1 (accession No. X03956). The PCR primers utilized added a HindIII site to the 5' end and a SmaI site at the 3' end of the molecule. The resulting about 1.05 kb PCR fragment was ligated into plasmid pUC19 that had previously been digested with HindIII and SmaI to form new plasmid pPPR001 that is schematically shown in FIG. 11.

2. Plasmid pATC954

Figure 12:
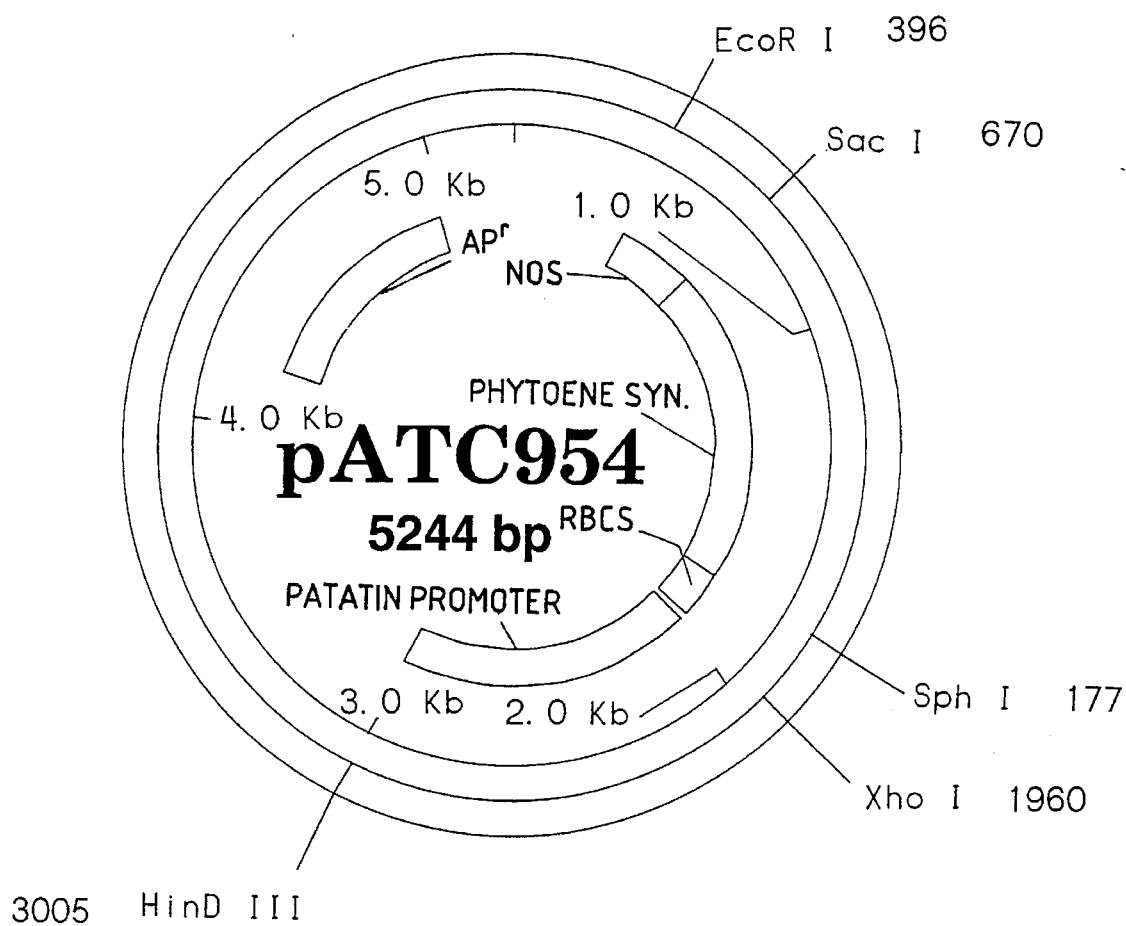
FIG. 12 schematically shows plasmid pATC954 that contains the gene for the RUBISCO/phytoene synthase conjugate polypeptide and nos terminator under the control of the patatin promoter of FIG. 11, as is shown in FIG. 3.

Previously discussed plasmid pATC921 was digested with XhoI, filled in with the Klenow fragment and four dNPTS, and then digested with EcoRI, resulting in removal of an about 1.56 kb DNA fragment containing the gene for the RUBISCO transit peptide and phytoene synthase and the nopaline synthase (nos) polyadenylation signal (terminator). This fragment was ligated into plasmid pPPR001 that had previously been digested with EcoRI and SmaI. The resulting plasmid was designated pATC954 that is schematically shown in FIG. 12. These procedures regenerated the XhoI site originally present in pATC921, whereas the SmaI site of plasmid pPPR001 was not regenerated.

3. Plasmid pATC956

Figure 13:
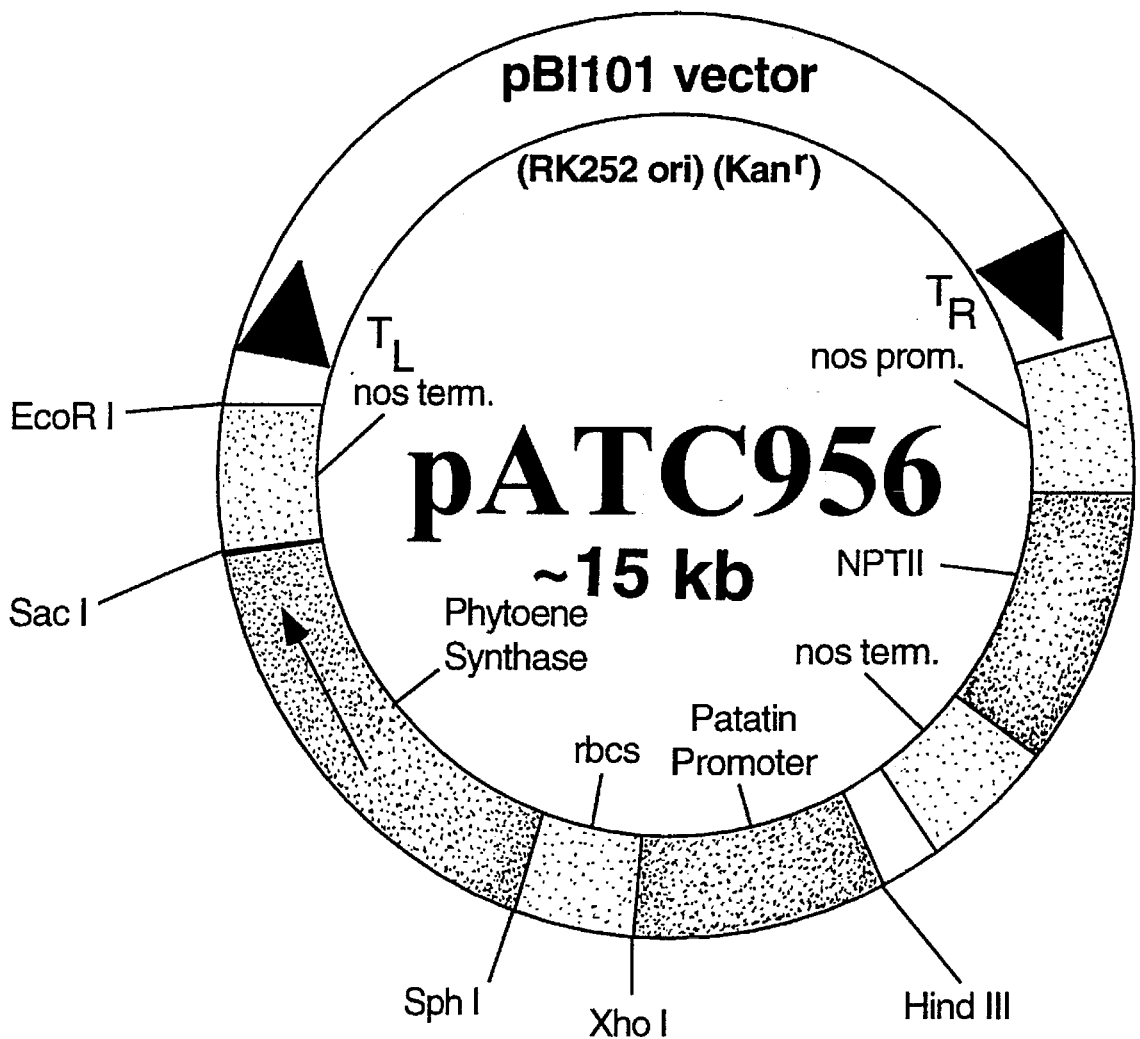
FIG. 13 schematically shows plasmid pATC956 that contains the genes for the patatin promoter-RUBISCO/phytoene synthase conjugate peptide and nos terminator of FIG. 12 cloned into commercially available plasmid pBI101.2, as is shown in FIG. 3.

Digestion of plasmid pATC954 with EcoRI and HindIII provided an about 2.6 kb DNA fragment that contained the patatin promoter, gene for the chimeric RUBISCO/phytoene synthase polypeptide conjugate and the nos terminator. This 2.6 kb fragment was ligated into binary plasmid pBI101.2 used in preparing plasmid pATC703, and which had been cut with EcoRI and HindIII. The resulting vector is referred to as plasmid pATC956 and is shown schematically in FIG. 13. Plasmid vector pATC956 is useful for transfection into *A. tumefaciens* and subsequently for transfecting potato plants that produce colored carotenoids in their tubers such as 88K3.58.

Carrying out that transformation with 88K3.58 potato calli and regeneration of plants as discussed by Twell et al. provides plants that appear normal in growth and morphology, and that produce tubers. The transformant tubers so produced exhibit enhanced accumulation of colored carotenoids relative to the untransformed plants when both are grown under the same conditions.

The foregoing description and the examples are intended as illustrative and are not to be taken as limiting. Still other variations within the spirit and scope of this invention are possible and will readily present themselves to those skilled in the art.

We claim:

1. A process for providing accumulation of a colored native carotenoid in a preselected storage organ of a transgenic higher plant that is enhanced compared to the accumulation of said colored native carotenoid in said storage organ of a non-transformed plant of the same type when both plants are grown under the same conditions that comprises the steps of growing said transformed plant to the maturity of said preselected storage organ, the genome of said transgenic plant containing (i) a DNA segment that encodes a chimeric polypeptide conjugate operatively linked to (ii) a promoter DNA segment that drives storage organ-enhanced expression of said chimeric polypeptide conjugate in a preselected storage organ of said transgenic plant, said chimeric polypeptide conjugate having an N-terminal plastid transit peptide portion whose C-terminus is peptide-bonded to the N-terminus of a non-higher plant phytoene synthase enzyme.

2. The process according to claim 1 wherein said preselected storage organ is selected from the group consisting of a root, seed, tuber and fruit.

3. The process according to claim 1 wherein said plant is selected from the group consisting of potato, tomato, carrot, melon, squash, red guava, passion fruit, mango, red papaya, avocado, cherry, tangerine, mandarin, palm, cucumber, apricot, peach and maize.

4. The process according to claim 1 wherein said plastid transit peptide portion is selected from the group consisting of the tobacco RUBISCO, petunia EPSP synthase, and pepper PSY gene transit peptides.

5. The process according to claim 1 wherein said promoter is a root- or tuber-enhanced promoter and said preselected storage organ is a root or tuber, respectively.

6. The process according to claim 5 wherein said root-enhanced promoter is selected from the group consisting of the mas, rape extensin, maize metallothionen-like protein, ASF-2 binding site-containing rbcS-3A, and base pairs −90 through +8 of the CAMV 35S promoter.

7. The process according to claim 5 wherein said tuber-enhanced promoter is the patatin promoter.

8. The process according to claim 1 wherein said chimeric polypeptide conjugate contains a phytoene synthase enzyme that is encoded by the crt B gene of *Erwinia herbicola*.

9. A process for providing accumulation of a colored native carotenoid in a preselected storage organ of a transgenic plant that is enhanced relative to the accumulation of said colored native carotenoid in said storage organ of a plant of the same type when both plants are grown under the same conditions that comprises the steps of:

(a) regenerating transgenic plant tissue into a transgenic plant, said transgenic plant tissue being plant tissue that is transformed with a recombinant DNA molecule that comprises a genomically integrating expression vector operatively linked to (i) a DNA segment that encodes a chimeric polypeptide conjugate and (ii) a promoter DNA segment that drives the storage organ-enhanced expression of said chimeric polypeptide conjugate in said preselected storage organ of a transgenic plant regenerated from said transgenic plant tissue, said chimeric polypeptide conjugate having an N-terminal plastid transit peptide portion whose C-terminus is linked to the N-terminus of a non-higher plant phytoene synthase enzyme; and (b) growing the transgenic plant to maturity of said storage organ.

10. The process according to claim 9 wherein said storage organ is selected from the group consisting of a root, seed, tuber and fruit.

11. The process according to claim 9 wherein said plant is selected from the group consisting of potato, tomato, carrot, melon, squash, red guava, passion fruit, mango, red papaya, avocado, cherry, tangerine, mandarin, palm, cucumber, apricot, peach and maize.

12. The process according to claim 9 wherein said plastid transit peptide portion is selected from the group consisting of the tobacco RUBISCO, petunia EPSP synthase, and pepper PSY gene transit peptides.

13. The process according to claim 9 wherein said promoter is a root- or tuber-enhanced promoter and said preselected storage organ is a root or tuber, respectively.

14. The process according to claim 13 wherein said root-enhanced promoter is selected from the group consisting of the mas, rape extensin, maize metallothionen-like protein, ASF-2 binding site-containing rbcS-3A, and base pairs −90 through +8 of the CAMV 35S promoter.

15. The process according to claim 13 wherein said tuber-enhanced promoter is the patatin promoter.

16. The process according to claim 9 wherein said chimeric polypeptide conjugate contains a phytoene synthase enzyme that is encoded by the crt B gene of *Erwinia herbicola*.

17. A process for providing accumulation of a colored native carotenoid in a preselected storage organ of a transgenic plant that is enhanced compared to the accumulation of said colored native carotenoid in said storage organ of a non-transformed plant of the same type when both plants are grown under the same conditions comprising the steps of:

(a) forming transgenic plant tissue by genomically transforming tissue of a plant that accumulates a colored carotenoid in a preselected storage organ with a recombinant DNA molecule that comprises an integrating vector operatively linked to (i) a DNA segment that encodes a chimeric polypeptide conjugate and (ii) a promoter DNA segment that drives the storage organ-enhanced expression of said chimeric polypeptide conjugate in said preselected storage organ of a transgenic plant regenerated from said transgenic plant tissue, said chimeric polypeptide conjugate having an N-terminal plastid transit peptide portion whose C-terminus is linked to the N-terminus of a non-higher plant phytoene synthase enzyme;

(b) regenerating said transgenic plant tissue into said transgenic plant having a storage organ; and (c) growing said transgenic plant to the maturity of said preselected storage organ.

18. The process according to claim 17 wherein said storage organ is selected from the group consisting of a root, seed, tuber and fruit.

19. The process according to claim 17 wherein said colored carotenoid is a carotene or a xanthophyll.

20. The process according to claim 17 wherein said plant tissue is obtained from a plant selected from the group consisting of potato, tomato, carrot, melon, squash, red guava, passion fruit, mango, red papaya, avocado, cherry, tangerine, mandarin, palm, cucumber, apricot, peach and maize.

21. The process according to claim 17 wherein said plastid transit peptide portion is selected from the group consisting of the tobacco RUBISCO, petunia EPSP synthase, and pepper PSY gene transit peptides.

22. The process according to claim 17 wherein said promoter is a root- or tuber-enhanced promoter and said preselected storage organ is a root or tuber, respectively.

23. The process according to claim 22 wherein said root-enhanced promoter is selected from the group consisting of the mas, rape extensin, maize metallothionen-like protein, ASF-2 binding site-containing rbcS-3A, and base pairs—90 through +8 of the CAMV 35S promoter.

24. The process according to claim 22 wherein said tuber-enhanced promoter is the patatin promoter.

25. The process according to claim 17 wherein said chimeric polypeptide conjugate contains a phytoene synthase enzyme that is encoded by the crtB gene of *Erwinia herbicola*.

26. A process for enhancing carotene or xanthophyll accumulation in a root of a transformed carrot that accumulates a carotene or xanthophyll in the root as a non-transformed plant comprising the steps of:

(a) forming transgenic carrot tissue by genomically transforming tissue of carrot that accumulates a carotene or xanthophyll in the root with recombinant DNA molecule that comprises an integrating vector operatively linked to (i) a DNA segment that encodes a chimeric polypeptide conjugate and (ii) a mas promoter DNA segment that drives the root-enhanced expression of said chimeric polypeptide conjugate in the root of a transgenic carrot plant regenerated from said transgenic carrot tissue, said chimeric polypeptide conjugate having an N-terminal RUBISCO transit peptide portion whose C-terminus is linked to the N-terminus of the *Erwinia herbicola* phytoene synthase enzyme;

(b) regenerating said transgenic carrot tissue into a transgenic carrot plant having a root; and (c) growing said transgenic carrot plant to the maturity of the root.

27. A transgenic plant that (a) has a genomic structural gene that encodes a chimeric polypeptide conjugate and (b) over-accumulates a colored native carotenoid in a preselected storage organ relative to the accumulation of colored native carotenoid in said storage organ in a non-transgenic plant of the same type, said chimeric polypeptide conjugate having an N-terminal plastid transit peptide portion whose C-terminus is linked to the N-terminus of a non-higher plant phytoene synthase enzyme.

28. The transgenic plant according to claim 27 wherein said storage organ is selected from the group consisting of a root, seed, tuber and fruit.

29. The transgenic plant according to claim 28 that is a carrot.

30. A transgenic plant that (a) has a genomic structural gene that encodes a chimeric polypeptide conjugate and (b) over-accumulates a colored native carotenoid in a preselected storage organ that is selected from the group consisting of a root, seed, tuber and fruit relative to the accumulation in said storage organ of a non-transgenic plant of the same type, said chimeric polypeptide conjugate having an N-terminal plastid transit peptide portion whose C-terminus is linked to the N-terminus of a non-higher plant phytoene synthase enzyme.

31. The transgenic plant according to claim 30 wherein said plastid transit peptide portion is the RUBISCO transit peptide.

32. The transgenic plant according to claim 30 wherein said non-higher plant that exhibits phytoene synthase enzyme is encoded by the crt B gene of *Erwinia herbicola*.

33. The transgenic plant according to claim 30 wherein said non-transgenic plant is selected from the group consisting of potato, tomato, carrot, melon, squash, red guava, passion fruit, mango, red papaya, avocado, cherry, tangerine, mandarin, palm, cucumber, apricot, peach and maize.

34. The transgenic plant according to claim 30 wherein said colored carotenoid is selected from the group consisting of a carotene and xanthophyll.

35. A transgenic carrot that (a) has a genomic structural gene that encodes a chimeric polypeptide conjugate and (b) over-accumulates a carotene or xanthophyll in the root relative to the accumulation of a non-transgenic carrot of the same type, said chimeric polypeptide conjugate having an N-terminal RUBISCO transit peptide portion whose C-terminus is linked to the N-terminus of the *Erwinia herbicola* phytoene synthase enzyme.

36. A transgenic plant seed capable of germinating into a transgenic plant that over accumulates a colored native carotenoid relative to a non-transgenic plant of the same type and hybrids derived therefrom, said seed and hybrids containing a genomic gene that encodes a chimeric polypeptide conjugate that is operably linked to a promoter that drives the storage organ-enhanced expression of said chimeric polypeptide conjugate in a preselected storage organ of a plant grown from said seed, said chimeric polypeptide conjugate having an N-terminal plastid transit peptide portion whose C-terminus is linked to the N-terminus of a non-higher plant phytoene synthase enzyme.

37. The transgenic plant seed according to claim 36 wherein said colored native carotenoid is selected from the group consisting of carotene and xanthophyll.

38. The transgenic plant seed according to claim 37 that is carrot seed.

* * * * *